(12) United States Patent
Rozbicki et al.

(10) Patent No.: US 9,885,934 B2
(45) Date of Patent: Feb. 6, 2018

(54) PORTABLE DEFECT MITIGATORS FOR ELECTROCHROMIC WINDOWS

(71) Applicant: View, Inc., Milpitas, CA (US)

(72) Inventors: Robert T. Rozbicki, Germantown, TN (US); Bruce Baxter, Virginia Beach, VA (US); Trevor Frank, San Jose, CA (US)

(73) Assignee: View, Inc., Milpitas, CA (US)

( * ) Notice: Subject to any disclaimer, the term of this patent is extended or adjusted under 35 U.S.C. 154(b) by 1061 days.

(21) Appl. No.: 13/859,623

(22) Filed: Apr. 9, 2013

(65) Prior Publication Data
US 2013/0306615 A1 Nov. 21, 2013

Related U.S. Application Data

(63) Continuation-in-part of application No. 13/610,612, filed on Sep. 11, 2012, now Pat. No. 9,507,232.

(60) Provisional application No. 61/534,712, filed on Sep. 14, 2011, provisional application No. 61/614,668, filed on Mar. 23, 2012.

(51) Int. Cl.
G02F 1/153 (2006.01)
G02B 7/32 (2006.01)
G01N 21/958 (2006.01)
G02F 1/1362 (2006.01)

(52) U.S. Cl.
CPC ........... *G02F 1/153* (2013.01); *G01N 21/958* (2013.01); *G02B 7/32* (2013.01); *G02F 1/136259* (2013.01)

(58) Field of Classification Search
CPC combination set(s) only.
See application file for complete search history.

(56) References Cited

U.S. PATENT DOCUMENTS

| | | |
|---|---|---|
| 3,271,286 A | 9/1966 | Lepselter |
| 3,521,941 A | 7/1970 | Deb et al. |
| 3,652,929 A | 3/1972 | Cushman |
| 4,166,918 A | 9/1979 | Nostrand et al. |
| 4,293,194 A | 10/1981 | Takahashi |
| 4,309,082 A | 1/1982 | Kohara et al. |
| 4,543,171 A | 9/1985 | Firester et al. |
| 4,570,046 A | 2/1986 | Melanson et al. |
| 4,806,496 A | 2/1989 | Suzuki et al. |

(Continued)

FOREIGN PATENT DOCUMENTS

| | | |
|---|---|---|
| CN | 1703653 A | 11/2005 |
| CN | 1755437 A | 4/2006 |

(Continued)

OTHER PUBLICATIONS

U.S. Office Action dated Feb. 8, 2016 in U.S. Appl. No. 13/610,612.
(Continued)

Primary Examiner — Anne M Antonucci
Assistant Examiner — Renee M Larose
(74) Attorney, Agent, or Firm — Weaver Austin Villeneuve & Sampson LLP; Brian D. Griedel

(57) ABSTRACT

Portable apparatus for identifying and mitigating defects in electronic devices disposed on substrates or windows are disclosed herein. Such defects can be visually perceived by the end user. The substrates or windows may include flat panel displays, photovoltaic windows, electrochromic devices, and the like, particularly electrochromic windows.

15 Claims, 29 Drawing Sheets

(56) References Cited

U.S. PATENT DOCUMENTS

| | | | |
|---|---|---|---|
| 4,937,423 A | 6/1990 | Yoshihara et al. | |
| 5,011,582 A | 4/1991 | Oshikawa et al. | |
| 5,017,755 A * | 5/1991 | Yahagi | G02F 1/13439 219/121.68 |
| 5,202,788 A | 4/1993 | Weppner | |
| 5,290,986 A | 3/1994 | Colon et al. | |
| 5,747,770 A | 5/1998 | Bogart | |
| 5,837,960 A | 11/1998 | Lewis et al. | |
| 5,907,383 A | 5/1999 | Kurihara et al. | |
| 6,225,640 B1 | 5/2001 | Glenn et al. | |
| 6,228,662 B1 | 5/2001 | Hayashi et al. | |
| 6,337,758 B1 | 1/2002 | Beteille et al. | |
| 6,750,662 B1 | 6/2004 | Van Der Heide | |
| 6,834,158 B1 | 12/2004 | Templeton | |
| 7,001,540 B2 | 2/2006 | Kloeppner | |
| 7,531,101 B2 | 5/2009 | Beteille | |
| 7,687,740 B2 | 3/2010 | Bruland et al. | |
| 8,045,146 B2 * | 10/2011 | Saito | G01N 21/8806 356/237.2 |
| 8,300,298 B2 | 10/2012 | Wang et al. | |
| 8,432,603 B2 | 4/2013 | Wang et al. | |
| 8,582,193 B2 | 11/2013 | Wang et al. | |
| 8,764,950 B2 | 7/2014 | Wang et al. | |
| 8,764,951 B2 | 7/2014 | Wang et al. | |
| 8,929,406 B2 * | 1/2015 | Chuang | G01N 21/84 372/21 |
| 9,507,232 B2 | 11/2016 | Rozbicki et al. | |
| 9,638,977 B2 | 5/2017 | Friedman et al. | |
| 2003/0081201 A1 * | 5/2003 | Shibata | G01N 21/33 356/237.2 |
| 2003/0103108 A1 | 6/2003 | Liu et al. | |
| 2003/0111447 A1 * | 6/2003 | Corkum | B23K 26/032 219/121.69 |
| 2004/0101981 A1 | 5/2004 | Morishita | |
| 2006/0001801 A1 | 1/2006 | Kim et al. | |
| 2006/0098264 A1 | 5/2006 | Park | |
| 2006/0193031 A1 | 8/2006 | Moore | |
| 2006/0197462 A1 | 9/2006 | Uchiyama et al. | |
| 2007/0081151 A1 * | 4/2007 | Shortt | G01N 21/47 356/237.2 |
| 2007/0092128 A1 | 4/2007 | Noy et al. | |
| 2007/0092129 A1 | 4/2007 | Sugiyama et al. | |
| 2007/0097481 A1 | 5/2007 | Burdis et al. | |
| 2007/0141360 A1 | 6/2007 | Beteille | |
| 2007/0289768 A1 | 12/2007 | Moore et al. | |
| 2008/0128286 A1 | 6/2008 | Wu et al. | |
| 2008/0178905 A1 | 7/2008 | Turner et al. | |
| 2008/0304130 A1 | 12/2008 | Nguyen | |
| 2008/0304131 A1 | 12/2008 | Nguyen | |
| 2009/0279079 A1 * | 11/2009 | Shibata | G01N 21/95623 356/237.3 |
| 2010/0074515 A1 | 3/2010 | Zhao et al. | |
| 2010/0243427 A1 | 9/2010 | Kozlowski et al. | |
| 2010/0245973 A1 | 9/2010 | Wang et al. | |
| 2011/0048614 A1 | 3/2011 | Veerasamy | |
| 2012/0026573 A1 | 2/2012 | Collins et al. | |
| 2012/0030121 A1 | 2/2012 | Grellier | |
| 2012/0302121 A1 * | 11/2012 | Sbar | B23K 26/0096 445/2 |
| 2013/0092679 A1 | 4/2013 | Rozbicki | |
| 2013/0258436 A1 | 10/2013 | Podbelski | |
| 2015/0077831 A1 | 3/2015 | Friedman et al. | |
| 2015/0097944 A1 | 4/2015 | Palm et al. | |
| 2015/0108102 A1 | 4/2015 | Martin | |
| 2017/0003566 A1 | 1/2017 | Friedman et al. | |
| 2017/0044057 A1 | 2/2017 | Rozbicki et al. | |

FOREIGN PATENT DOCUMENTS

| | | |
|---|---|---|
| CN | 101274391 A | 10/2008 |
| CN | 101697040 A | 4/2010 |
| EP | 0958882 A2 | 11/1999 |
| EP | 2036652 A1 | 3/2009 |
| JP | S56-35125 A | 4/1981 |
| JP | S58-93591 A | 6/1983 |
| JP | H07-028099 A | 1/1995 |
| JP | H10-58169 A | 3/1998 |
| JP | 2001-066418 | 3/2001 |
| JP | 2007-205724 | 8/2007 |
| JP | 2009-198230 | 9/2009 |
| KR | 10-2007-0099216 A | 10/2007 |
| KR | 10-0838656 | 6/2008 |
| KR | 10-2011-0084703 A | 7/2011 |
| KR | 10-2012-0127171 A | 11/2012 |
| TW | 201116918 A | 5/2011 |
| WO | WO 2004/034138 A1 | 4/2004 |
| WO | WO 2010-120535 | 10/2010 |
| WO | WO 2012154320 | 11/2012 |
| WO | WO 2013/039915 A1 | 3/2013 |
| WO | WO 2013/138535 A1 | 9/2013 |
| WO | WO 2013/173591 A1 | 11/2013 |

OTHER PUBLICATIONS

U.S. Appl. No. 13/610,612, filed Sep. 11, 2012.
U.S. Appl. No. 12/336,466, filed Dec. 16, 2008.
U.S. Office Action dated Jun. 12, 2012 in U.S. Appl. No. 12/336,466.
U.S. Final Office Action dated Oct. 30, 2012 in U.S. Appl. No. 12/336,466.
International Search Report dated Jan. 31, 2013 for PCT/US2012/054665.
U.S. Office Action dated Sep. 13, 2013 in U.S. Appl. No. 12/336,466.
U.S. Office Action dated May 9, 2014 in U.S. Appl. No. 12/336,466.
U.S. Final Office Action dated Mar. 18, 2015 in U.S. Appl. No. 12/336,466.
International Preliminary Report on Patentability dated Mar. 27, 2014 in PCT Application No. PCT/US2012/054665.
International Search Report dated Aug. 4, 2014 in PCT Application No. PCT/US2014/033059.
International Preliminary Report on Patentability dated Jul. 29, 2015 in PCT Application No. PCT/US2014/033059.
International Search Report dated Jun. 4, 2013 in PCT Application No. PCT/US2013/031098.
International Preliminary Report on Patentability dated Sep. 25, 2014 in PCT Application No. PCT/US2013/031098.
International Search Report and Written Opinion for PCT/US2013/041365 dated Aug. 27, 2013.
International Preliminary Report on Patentability for PCT/US2013/041365 dated Nov. 27, 2014.
Extended European Search Report dated Jun. 18, 2015 for EP Application No. 12832253.4.
Extended European Search Report dated Sep. 21, 2015 for EP Application No. 13760591.1.
U.S. Notice of Allowance dated Jul. 19, 2016 in U.S. Appl. No. 13/610,612.
U.S. Notice of Allowance dated Sep. 14, 2016 (supplemental) in U.S. Appl. No. 13/610,612.
U.S. Office Action dated Jul. 5, 2016 in U.S. Appl. No. 12/336,466.
U.S. Office Action dated Mar. 11, 2016 in U.S. Appl. No. 14/384,146.
U.S. Notice of Allowance dated Aug. 15, 2016 in U.S. Appl. No. 14/384,146.
EP Partial Supplementary Search Report dated Jan. 25, 2016 for EP Application No. 13791156.6.
EP Extended Search Report dated May 13, 2016 for EP Application No. 13791156.6.
CN Office Action dated Oct. 13, 2015 in CN Application No. 201380025529.2.
TW Office Action dated Apr. 8, 2016 in TW Application No. 101133555.
U.S. Office Action dated Jan. 12, 2017 in U.S. Appl. No. 14/384,146.
U.S. Notice of Allowance dated Mar. 7, 2017 in U.S. Appl. No. 14/384,146.
U.S. Office Action dated Jun. 12, 2017 in U.S. Appl. No. 14/398,117.

(56) References Cited

OTHER PUBLICATIONS

EP Office Action dated Oct. 7, 2016 in EP Application No. 13760591.1.
CN Office Action dated Aug. 31, 2016 in CN Application No. 201380025529.2.
CN Office Action dated Mar. 13, 2017 in CN Application No. 201380025529.2.
U.S. Final Office Action dated Mar. 14, 2017 in U.S. Appl. No. 12/336,466.
U.S. Office Action dated Nov. 30, 2017 in U.S. Appl. No. 12/336,466.

* cited by examiner

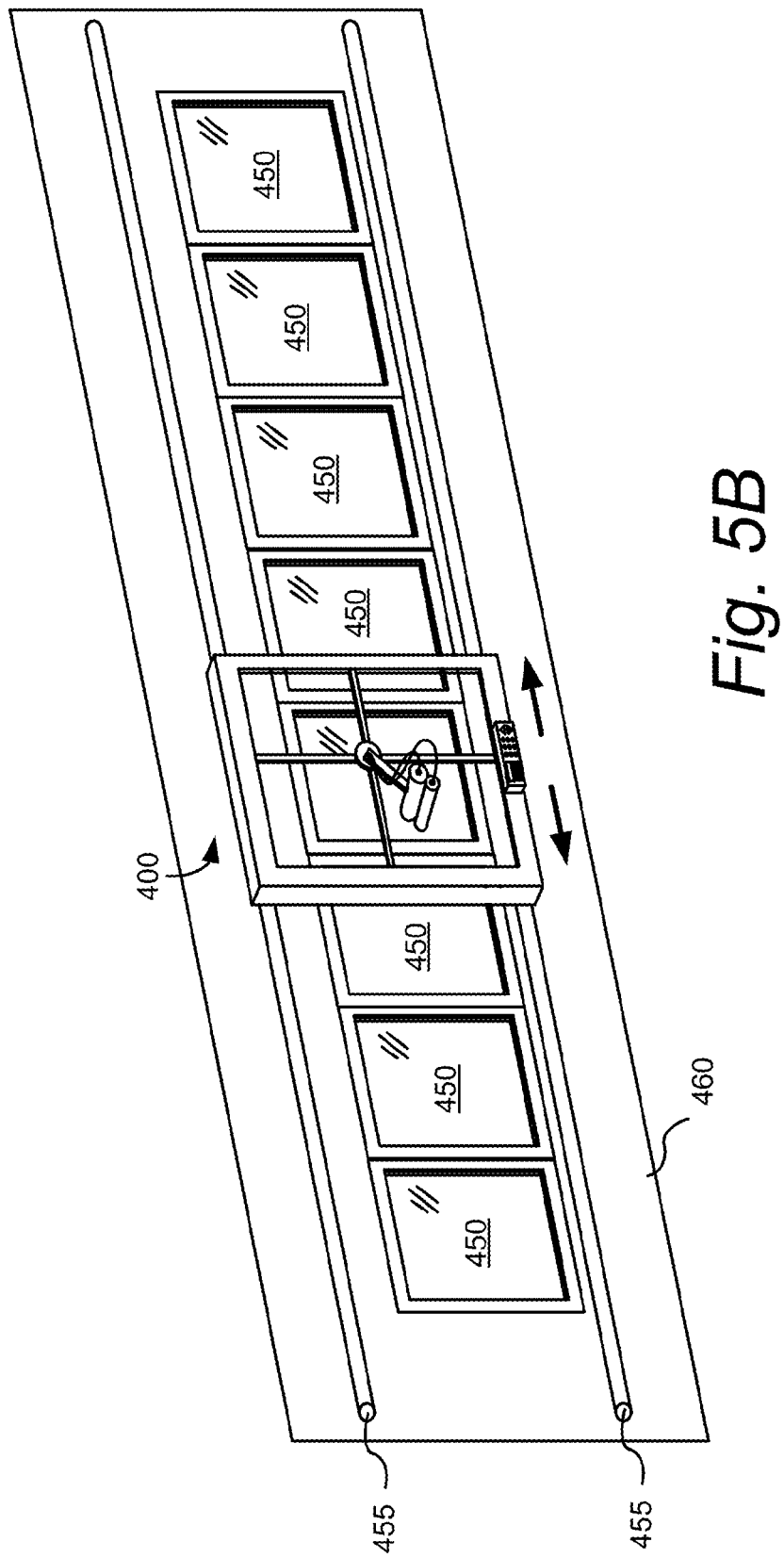

PORTABLE DEFECT MITIGATORS FOR ELECTROCHROMIC WINDOWS

CROSS-REFERENCES TO RELATED APPLICATIONS

This application is a continuation-in-part application of U.S. patent application Ser. No. 13/610,612 filed on Sep. 11, 2012, which is a non-provisional application of and claims priority to both U.S. Provisional Patent Application No. 61/534,712 filed on Sep. 14, 2011 and U.S. Provisional Patent Application No. 61/614,668 filed on Mar. 23, 2012. All of these applications are hereby incorporated by reference in their entirety and for all purposes.

FIELD

The present disclosure concerns apparatus, systems, and methods for mitigating defects in electronic devices on substrates, e.g., where such defects can be visually perceived by the end user, such as flat panel displays, photovoltaic windows, electrochromic devices, and the like, particularly electrochromic windows.

BACKGROUND

Electrochromism is a phenomenon in which a material exhibits a reversible electrochemically-mediated change in an optical property when placed in a different electronic state, typically by being subjected to a voltage change. The optical property is typically one or more of color, transmittance, absorbance, and reflectance. While electrochromism was discovered in the 1960s, electrochromic devices still unfortunately suffer various problems and have not begun to realize their full commercial potential.

Electrochromic materials may be incorporated into, for example, windows and mirrors. The color, transmittance, absorbance, and/or reflectance of such windows and mirrors may be changed by inducing a change in the electrochromic material. However, advancements in electrochromic technology, apparatus, and related methods of making and/or using them, are needed because conventional electrochromic windows suffer from, for example, high defectivity and low versatility.

Electrochromic windows are made by forming an electrochromic device on a pane of transparent material. During production, the electrochromic device on the pane is scrutinized for any defects that would cause visual distortions or anomalies to the end user of the window. These defects are then mitigated. Mitigation may include isolating short type defects using probes and then "zapping" the short defect by applying a localized electric arc to overload and destroy the short conduction path. Other methods of mitigation include, for example, identifying visual defects and then circumscribing each defect with a laser to electronically isolate the defect and thereby lower or eliminate the visual effect the defect would create when the window is in a colored state. Similar mitigation efforts are made for other electronic devices on substrates where such defects can be visually perceived by the end user, such as flat panel displays. The electronic device may be analyzed for defects on one machine and then the defects mitigated on another machine in a production facility setting. Such defect detection and mitigation apparatus for flat panel displays are commercially available, for example, under the trade names of Array-Checker™ and ArraySaver™ which are made by Orbotech Inc. of Billerica, Mass.

SUMMARY

Systems, methods, an apparatus for identifying and mitigating defects in electronic devices on substrates, which may be included in flat panel displays, photovoltaic windows, electrochromic windows, and the like. In some cases, the apparatus may be a portable defect mitigator that can be easily transported to identify and mitigate a defect in the electronic device located in the field (e.g., an electrochromic window installed in a building). The portable defect mitigator may be a hand-held operated design that can be easily maneuvered and affixed to the surface of the window during the procedure.

In the field, a window may be subjected to forces (e.g., wind gusts) that can bend or otherwise deform the window. Certain embodiments include a dynamic autofocus system for automatically focusing a laser during mitigation of a defect in an electronic device of a deforming window. The dynamic autofocus system has a focal lens for focusing the collimated light from a laser mitigating the defect. The dynamic autofocus system also has a detector mechanism (e.g., triangulation sensor) for measuring a separation distance to the surface of the electronic device. The detector mechanism takes this measurement at one or more sample times. The dynamic autofocus system also has a lens positioning mechanism for moving the lens to about a focal length from the surface of the electronic device based on the separation distance measured at the sample time. The dynamic autofocus system also has a processor that can send a signal to the lens positioning mechanism to move the focal lens. In one case, the detector mechanism also measures a rate of change of the separation distance at the sample time. The processor predicts the separation distance at a future time based on the separation distance and its rate of change measured at the sample time. The lens positioning mechanism moves the lens to about the focal length based on the predicted separation distance at the future time determined from the measured separation distance and rate of change at the sample time.

In one aspect, the portable defect mitigator may include a vacuum engagement system for affixing the mitigator to a window surface. The vacuum engagement system includes a plurality of isolated recesses and a groove around each of the recesses. The system also includes O-rings, each O-ring is configured to fit within one of the grooves. Each of the recesses is vacuum sealed with the O-ring to form a vacuum chamber with the window surface. The vacuum engagement system may a set of valves. Each valve is configured to control vacuum in one of the vacuum chambers. The valves may be independently controlled.

In some embodiments, a portable defect mitigator includes a first mechanism configured to detect the defect, a second mechanism configured to mitigate the defect, and a dichroic mirror for receiving collimated illumination from the first mechanism and the second mechanism. The portable defect mitigator also includes a reflective mirror for receiving collimated illumination along a coaxial path from the dichroic mirror and a focal lens receiving collimated illumination reflected from the mirror and focusing the illumination to the electronic device to image and mitigate the defect. In some cases, the portable defect mitigator may include a pivoting mechanism for pivoting the mirror and focal lens about a pivot point to focus the illumination at an angle to a plane at a surface of the electronic device. For example, the focal lens can focus the illumination to a focal point at a corner of an insulated glass unit. As another example, the focal lens can focus the illumination to a focal point under a spacer of an insulated glass unit.

One embodiment is a method of mitigating a defect in an electronic device on a window using a portable defect mitigator. The method includes mounting the portable defect mitigator to a surface of the window. The method also includes focusing a laser on the surface of the electronic device and identifying one or more defects in a field of view. The method also includes mitigating a selected defect using a laser based on a selected scribe pattern.

In embodiments, the portable defect mitigator may include one or more subsystems with a variety of functionalities. One subsystem is an X-Y stage for increasing the field of view of the mitigating laser and the imaging device. Another subsystem is a Z-stage for moving the focal point of the laser and/or imaging device. Another subsystem is a tether system for tethering the portable defect mitigator for added safety. Another subsystem is a vacuum engagement system for affixing the portable defect mitigator to the surface of the window. Another subsystem is a dynamic autofocus system. Another subsystem includes imaging and mitigation systems which share a common axis from a dichroic mirror through the focal lens and onto the window surface. Another subsystem is a pivot system for pivoting the optics in a portable defect mitigator mounted to the window in order to image and mitigate defects at the corners or underneath a spacer of an IGU. Another subsystem is a light tight hand-held chassis and/or a case-like structure separate from the chassis. Another subsystem is a tracking stylus for manually inputting defect locations. Another subsystem is a beam blocker.

These and other features and embodiments will be described in more detail below with reference to the drawings.

BRIEF DESCRIPTION OF THE FIGURES

FIG. 5B depicts a rail or track system for apparatus as described herein.

DETAILED DESCRIPTION

Electrochromic Devices

Figure 1A:
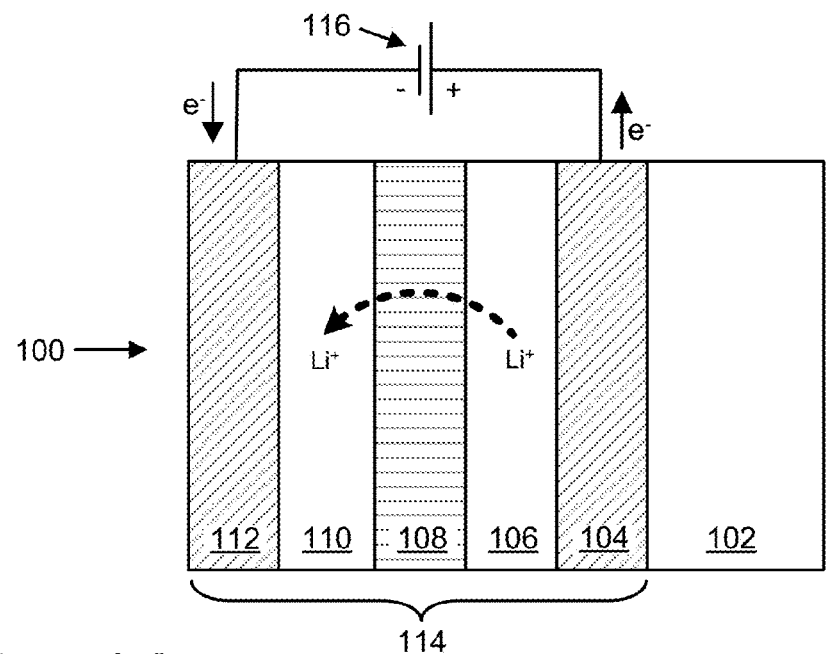
FIGS. 1A and 1B depict the structure and function of electrochromic devices.
Figure 1B:
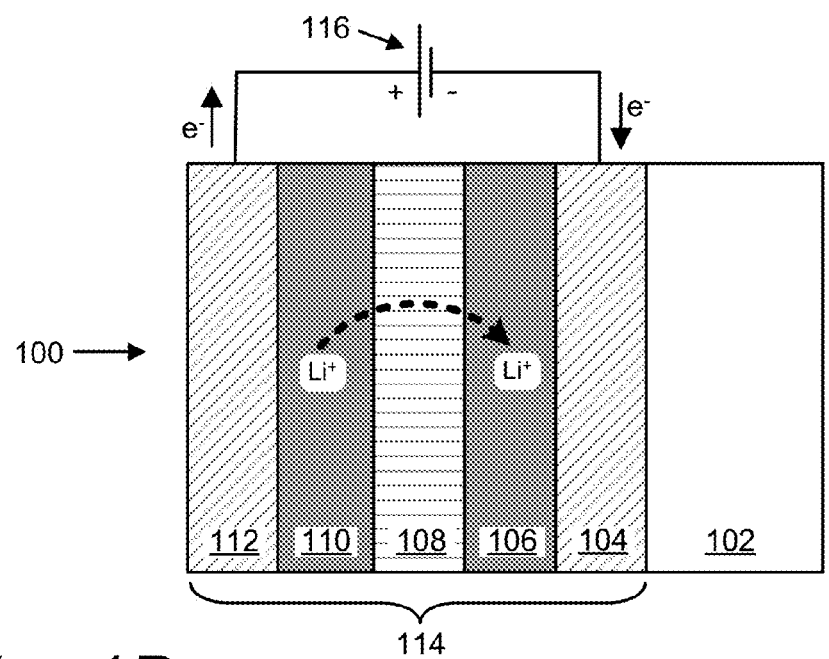

FIGS. 1A and 1B are schematic cross-sections of an electrochromic device, 100, showing a common structural motif for such devices, and further, the function of such devices is summarized below. Electrochromic device 100 includes a substrate 102, a conductive layer (CL) 104, an electrochromic layer (EC) 106, an ion conducting (electrically resistive) layer (IC) 108, a counter electrode layer (CE) 110, and another conductive layer (CL) 112. Elements 104, 106, 108, 110, and 112 are collectively referred to as an electrochromic stack, 114. A voltage source, 116, operable to apply an electric potential across electrochromic stack 112 effects the transition of the electrochromic device from, e.g., a bleached state (refer to FIG. 1A) to a colored state (refer to FIG. 1B). The order of layers may be reversed with respect to the substrate. That is, the layers may be in the following order: substrate, conductive layer, counter electrode layer, ion conducting layer, electrochromic material layer, and conductive layer. The conductive layers commonly comprise transparent conductive materials, such as metal oxides, alloy oxides, and doped versions thereof, and are commonly referred to as "TCO" layers because they are made from transparent conducting oxides. Device 100 is meant for illustrative purposes, in order to understand the context of embodiments described herein. Methods and apparatus described herein are used to identify and mitigate defects in electrochromic devices, regardless of the structural motif of the electrochromic device, so long as there is a stacked device structure that functions similarly to device 100, that is, devices that can have visual defects that can be mitigated as described herein.

During normal operation, electrochromic devices such as 100 reversibly cycle between a bleached state and a colored state. As depicted in FIG. 1A, in the bleached state, a potential is applied across the electrodes (transparent conductor layers 104 and 112) of electrochromic stack 114 such that available ions (e.g. lithium ions) in the stack that would otherwise cause electrochromic material 106 to be in the colored state reside primarily in the counter electrode 110, and thus electrochromic layer 106 is in a bleached state. In certain electrochromic devices, when loaded with the available ions, counter electrode layer 110 is also in a bleached state (thus it can be thought of as an ion storage area of the device).

Referring to FIG. 1B, when the potential on the electrochromic stack is reversed, the ions are transported across ion conducting layer 108 to electrochromic layer 106 and cause the material to enter the colored state. In certain electrochromic devices, the depletion of ions from the counter electrode material causes it to color also (as depicted, thus in this example counter electrode layer 110 is a lithium storage area when the device is bleached, and also functions to color the device when the ions leave layer 110). Thus, there is a synergistic effect where the transition to colored states for both layers 106 and 110 are additive toward reducing the amount of light transmitted through the stack. When the voltage is no longer applied to device 100, ions travel from electrochromic layer 106, through the ion conducting layer 108, and back into counter electrode layer 110.

Electrochromic devices such as described in relation to FIGS. 1A and 1B are used to fabricate, for example, electrochromic windows. For example, substrate 102 may be architectural glass upon which electrochromic devices are fabricated. Architectural glass is glass that is used as a building material. Architectural glass is typically used in commercial buildings, but may also be used in residential buildings, and typically, though not necessarily, separates an indoor environment from an outdoor environment. In certain embodiments, architectural glass is at least 20 inches by 20 inches, and can be much larger, e.g., as large as about 72 inches by 120 inches.

As larger and larger substrates are used for electrochromic windows it is desirable to minimize defects in the electrochromic device, because otherwise the performance and visual quality of the electrochromic windows will suffer. Even if defects are minimized, there will be some defects in the final product that must be mitigated. Understanding the needs addressed by embodiments described herein requires a better understanding of defectivity in electrochromic windows.

Defectivity in Electrochromic Windows

As used herein, the term "defect" refers to a defective point or region of an electrochromic device. Defects may be caused by electrical shorts or by pinholes. Further, defects may be characterized as visible or non-visible. In general, a defect in an electrochromic device, and sometimes an area around the defect, does not change optical state (e.g., color) in response to an applied potential that is sufficient to cause non-defective regions of the electrochromic device to color or otherwise change optical state. Often a defect will be manifest as visually discernible anomalies in the electrochromic window or other device. Such defects are referred to herein as "visible" defects. Other defects are so small that they are not visually noticeable to the observer in normal use (e.g., such defects do not produce a noticeable light point or "pinhole" when the device is in the colored state during daytime).

A short is a localized electronically conductive pathway spanning the ion conducting layer (e.g., an electronically conductive pathway between the two TCO layers). Typically, a defect causing a visible short will have a physical dimension of about 3 micrometers, sometimes less, which is a relatively small defect from a visual perspective. However, these relatively small defects result in a visual anomaly, the halo, in the colored electrochromic window that are, for example, about 1 centimeter in diameter, sometimes larger. Halos can be reduced significantly by isolating the defect, for example by circumscribing the defect via a laser scribe or by ablating the material directly without circumscribing it. For example, a circular, oval, triangular, rectangular, or other shaped perimeter is ablated around the shorting defect thus electrically isolating it from the rest of the functioning device. The circumscription may be only tens, a hundred, or up to a few hundred micrometers in diameter. By circumscribing, and thus electrically isolating the defect, the visible short will resemble only a small point of light to the naked eye when the window is colored and there is sufficient light on the other side of the window. When ablated directly, without circumscription, there remains no EC device material in the area where the electrical short defect once resided. Rather, there is a hole through the device and at the base of the hole is, for example, the float glass or the diffusion barrier or the lower transparent electrode material, or a mixture thereof. Since these materials are all transparent, light may pass through the base of the hole in the device.

Depending on the diameter of a circumscribed defect, and the width of the laser beam, circumscribed pinholes may also have little or no electrochromic material remaining within the circumscription (as the circumscription is typically, though not necessarily, made as small as possible). Such mitigated short defects manifest as pin points of light against the colored device, thus these points of light are commonly referred to as "pinholes." Isolation of an electrical short by circumscribing or direct ablation would be an example of a man-made pinhole, one purposely formed to convert a halo into a much smaller visual defect. However, pinholes may also arise as a natural result of defects in the optical device.

A pinhole is a region where one or more layers of the electrochromic device are missing or damaged so that electrochromism is not exhibited. Pinholes are not electrical shorts, and, as described above, they may be the result of mitigating an electrical short in the device. A pinhole may have a defect dimension of between about 25 micrometers and about 300 micrometers, typically between about 50 micrometers and about 150 micrometers, thus it is much harder to discern visually than a halo. Typically, in order to reduce the visible perception of pinholes resulting from mitigation of halos, one will limit the size of a purposely-created pinhole to about 100 micrometers or less.

| Particle Location | Worst Case Failure | Effect |
| --- | --- | --- |
| on substrate | pops off leaving pinhole | pinhole |
| on TEC | pops off allowing ITO-TEC short | visible short voltage drop |
| on EC | leakage across IC | visible short voltage drop |
| on IC | pops off leaving pinhole | pinhole |
| on CE | pops off leaving pinhole | pinhole |

In some cases, an electrical short is created by a conductive particle lodging in and/or across the ion conducting layer, thereby causing an electronic path between the counter electrode layer and the electrochromic layer or the TCO associated with either one of them. A defect may also be caused by a particle on the substrate on which the electrochromic stack is fabricated. When such a particle causes layer delamination due to stresses imparted by the particle, this is sometimes called "pop-off." In other instances, the layers do not adhere to the substrate properly and delaminate, interrupting the flow of ions and/or electrical current within the device. These types of defects are described in more detail below in relation to FIGS. 2 and 3A-3C. A delamination or pop-off defect can lead to a short if it occurs before a TCO or associated EC or CE is deposited. In such cases, the subsequently deposited TCO or EC/CE layer will directly contact an underlying TCO or CE/EC layer providing direct electronic conductive pathway. A few examples of defect sources are presented in the table below. The table below is intended to provide examples of mechanisms that lead to the different types of visible and non-visible defects. Additional factors exist which may influence how the EC window responds to a defect within the stack.

As noted above, in the case of a visible short the defect will appear as a light central region (when the device is in the colored state) with a diffuse boundary such that the device gradually darkens with distance from the center of the short. If there are a significant number of electrical shorts (visible or non-visible) concentrated in an area of an electrochromic device, they may collectively impact a broad region of the device whereby the device cannot switch in such region. This is because the potential difference between the EC and CE layers in such regions cannot attain a threshold level required to drive ions across the ion conductive layer. It should be understood that leakage current may result from sources other than short-type defects. Such other sources include broad-based leakage across the ion conducting layer and edge defects such as roll off defects as described elsewhere herein and scribe line defects. The emphasis here is on leakage caused only by points of electrical shorting across the ion conducting layer in the interior regions of the electrochromic device. These shorts cause visible defects that must be minimized and/or mitigated for the electrochromic pane to be acceptable for use in an electrochromic window. Conventionally, the visual defects are identified and mitigated prior to assembly of the pane into an insulated glass unit (IGU). Methods described herein allow identification and mitigation after the pane is fabricated into an IGU and also after installed in a building or, for example, after the pane is installed in an automobile.

Since an IGU may include more than two glass panes assembled into a unit (e.g. a triple pane unit), and for electrochromic windows specifically may include electrical leads for connecting the electrochromic glass to a voltage source, switches and the like, the term "window unit" is used to convey a more simple sub-assembly. That is, for the purposes of this invention, an IGU may include more components than a window unit. The most basic assembly of a window unit is two substrates (panes or glazings) with a sealing separator in between and registered with the two substrates.

Figure 2:
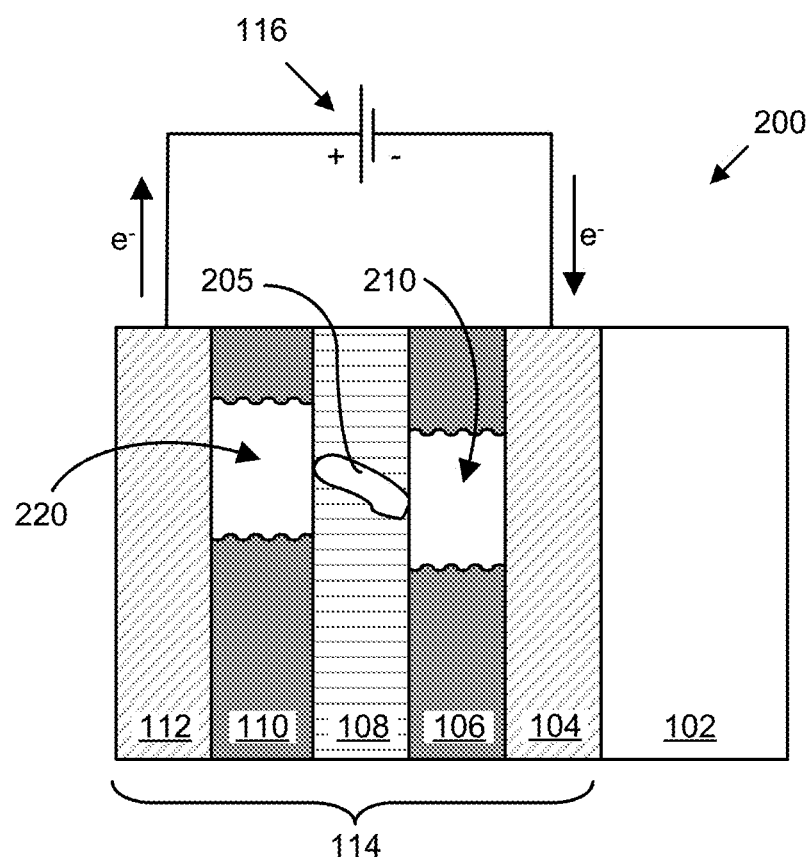
FIG. 2 depicts a particle defect in an electrochromic device.

FIG. 2 is a schematic cross-section of an electrochromic device, 200, with a particle, 205, in the ion conducting layer causing a localized defect in the device. In this example, electrochromic device 200 includes the same layers as described in relation to FIGS. 1A and 1B. Voltage source 116 is configured to apply a potential to electrochromic stack 114 as described above, through suitable connections (e.g., bus bars) to conductive layers 104 and 112.

In this example, ion conducting layer 108 includes a conductive particle, 205, or other artifact causing a defect. Conductive particle 205 results in a short between electrochromic layer 106 and counter electrode layer 110. In this example, particle 205 spans the thickness of the IC layer 108. Particle 205 physically impedes the flow of ions between electrochromic layer 106 and counter electrode layer 110, and also, due to its electrical conductivity, allows electrons to pass locally between the layers, resulting in a transparent region 210 in electrochromic layer 106 and a transparent region 220 in counter electrode layer 110. Transparent region 210 exists when the remainder of layers 110 and 106 are in the colored state. That is, if electrochromic device 200 is in the colored state, conductive particle 205 renders regions 210 and 220 of the electrochromic device unable to enter into the colored state. Sometimes such visible defect regions are referred to as "constellations" or "halos" because they appear as a series of bright spots (or stars) against a dark background (the remainder of the device being in the colored state). Humans will naturally direct their attention to the halos and often find them distracting or unattractive. Embodiments described herein identify and mitigate such visible defects. Pinhole defects may or may not be deemed worthy of repair, as they can be nearly indiscernible to the naked eye by most observers.

It should be noted that defect mitigators described herein may have optical detection components that allow detection of defects not discernible to the human eye. Moreover, the mitigation components described herein can repair such defects. Embodiments described herein are thus not limited to portable defect mitigators that detect and repair defects visually discernible to the human eye; however, visually discernible defects are of most concern from an end user perspective. Non-visually discernible defects can lead to poor device performance in the aggregate due to their associated leakage current, and thus may also be mitigated using apparatus and methods as described herein.

As mentioned above, visible short defects can also be caused by particles popping off, e.g. during or after fabrication of the electrochromic device, thereby creating damaged areas in the electrochromic stack, through one or more layers of the stack. Pop-off defects are described in more detail below.

Figure 3A:
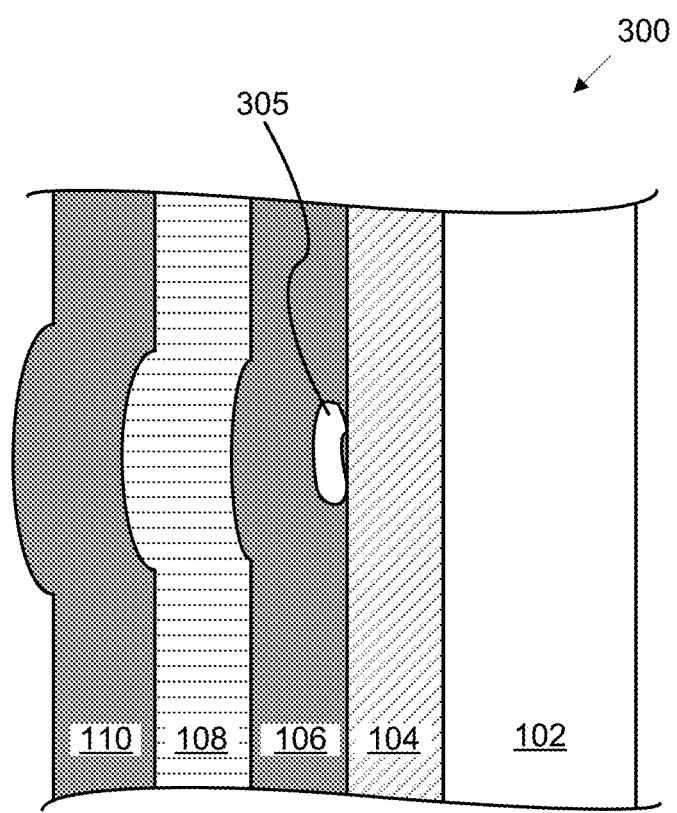
FIGS. 3A-3C depict aspects of formation of a pop-off defect.

FIG. 3A is a schematic cross-section of an electrochromic device, 300, with a particle 305 or other debris on conductive layer 104 prior to depositing the remainder of the electrochromic stack. Electrochromic device 300 includes the same components as electrochromic device 100. Particle 305 causes the layers in the electrochromic stack 114 to bulge in the region of particle 305, due to conformal layers 106-110 being deposited sequentially over particle 305 as depicted (in this example, conductive layer 112 has not yet been deposited). While not wishing to be bound by a particular theory, it is believed that layering over such particles, given the relatively thin nature of the layers, can cause stress in the area where the bulges are formed. More particularly, in each layer, around the perimeter of the bulged region, there can be defects in the layer, e.g. in the lattice arrangement or on a more macroscopic level, cracks or voids. One consequence of these defects would be, for example, an electrical short between electrochromic layer 106 and counter electrode layer 110 and/or loss of ion conductivity in layer 108. These defects are not depicted in FIG. 3A, however.

Figure 3B:
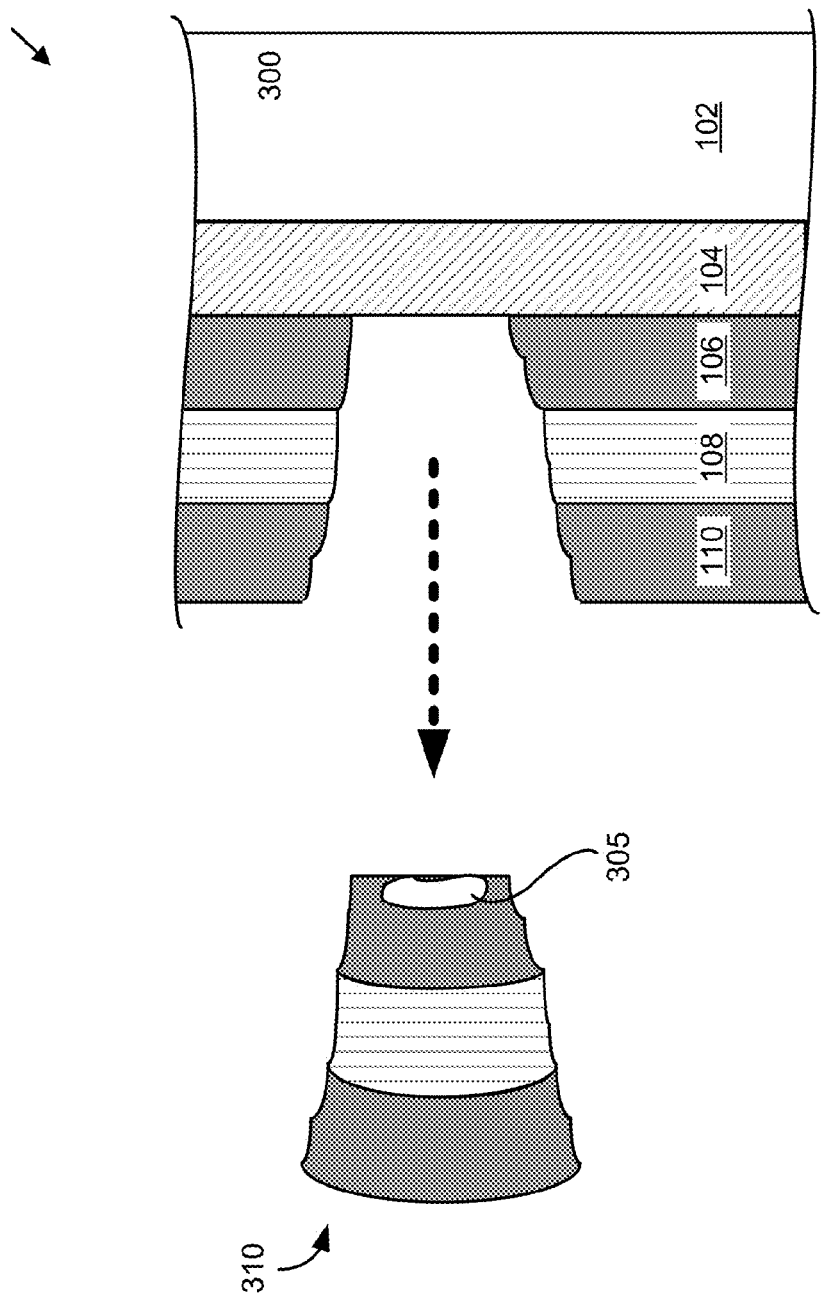
Figure 3C:
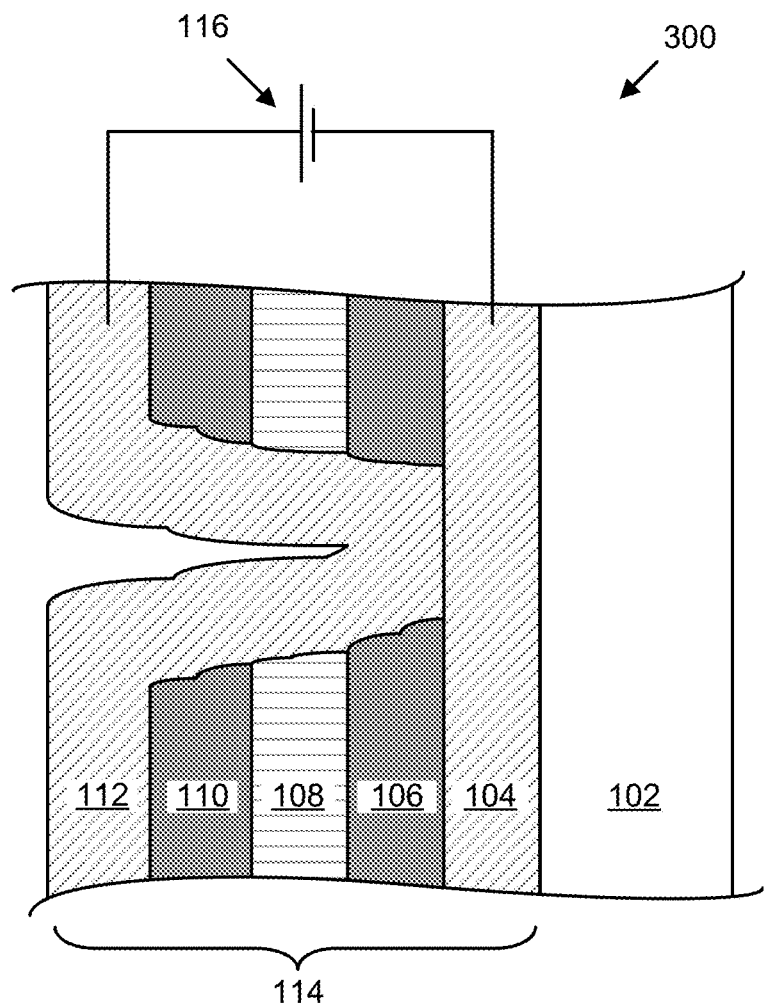

Referring to FIG. 3B, another consequence of defects caused by particle 305 is called a "pop-off" In this example, prior to deposition of conductive layer 112, a portion above the conductive layer 104 in the region of particle 305 breaks loose, carrying with it portions of electrochromic layer 106, ion conducting layer 108, and counter electrode layer 110. The "pop-off" is piece 310, which includes particle 305, a portion of electrochromic layer 106, as well as ion conducting layer 108 and counter electrode layer 110. The result is an exposed area of conductive layer 104 at the bottom of the trench left when piece 310 popped out of the layered stack of materials. Referring to FIG. 3C, after pop-off and once conductive layer 112 is deposited, an electrical short is formed where conductive layer 112 comes in contact with conductive layer 104. This electrical short would leave a transparent region in electrochromic device 300 when it is in the colored state, similar in appearance to the visual defect created by the short described above in relation to FIG. 2.

Pop-off defects due to particles or debris on the substrate, ion conducting layer, and on the counter electrode layer may also cause pinhole defects. Also, if a contaminate particle is large enough and does not cause a pop-off, it might be visible when the electrochromic device is in the bleached state.

The description above, as described in relation to FIGS. 1A, 1B, 2, and 3A-C, presumes that there is a distinct ion conducting (electronically resistive) layer sandwiched between an electrochromic layer and a counter electrode layer in electrochromic devices. The description is only meant to be illustrative of how a particle can create a short related defect. That is, there are electrochromic devices where a distinct electronically resistive and ion conducting layer does not exist, but rather an interfacial region that serves as an ion conductive layer exists at the interface of the electrochromic and counter electrode layers. Electrochromic devices having this architecture are described in U.S. patent application Ser. No. 12/772,055 filed Apr. 30, 2010, Ser. No. 12/772,075 filed Apr. 30, 2010, Ser. No. 12/814,277 filed Jun. 11, 2010, Ser. No. 12/814,279 filed Jun. 11, 2010 and Ser. No. 13/166,537 filed Jun. 22, 2011, each entitled, "Electrochromic Devices," each having inventors Wang et al., and each hereby incorporated by reference in their entirety. Thus particles can cause shorting defects in these devices as well, e.g., where the particle exists at and/or crosses the interface between the electrochromic and counter electrode layers and/or creates pop-off type defects as described. Such devices are also susceptible to other defect types described herein, despite not having a distinct IC layer as in conventional devices.

Thus, there are three types of defects are of primary concern with regard to electrochromic windows: (1) visible pinholes, (2) visible shorts, and (3) non-visible shorts. A visible pinhole will have a defect dimension of at least about 100 µm, and manifest as a very small point of light when the window is colored, sometimes barely discernible to the naked eye, but visible upon close scrutiny. Typically, though not necessarily, a visible short will have defect dimension of at least about 3 micrometers resulting in a region, e.g. of about 1 cm in diameter, often referred to as a "halo," where the electrochromic effect is perceptibly diminished. These halo regions can be reduced significantly by isolating the defect causing the visible short so that to the naked eye the visible short will resemble only a visible pinhole. Non-visible shorts can affect switching performance of the electrochromic device, by contributing to the overall leakage current of the device, but do not create discernible points of light or halos when the window is in a colored state.

Embodiments described herein include apparatus and methods where visible defects are identified and mitigated. In certain embodiments, the visible defect is due to a visible short, i.e., a visible defect that produces a halo is identified and mitigated. Visible short defects that produce halos are described in more detail below.

Visible shorts produce a halo when the device is darkened. A halo is a region in the device where an electrical short across the electrochromic stack causes an area around the short to drain current into the short and therefore the area surrounding the short is not darkened. As mentioned, these regions can be up to about 1 cm in diameter, and thus present a problem by making the electrochromic window, when colored, unattractive to the observer. This frustrates the purpose of having windows that can operate in a colored mode.

Conventionally visible short defects are mitigated after fabrication of the electrochromic device, but while still in the production facility, for example, prior to installation in an IGU. For example, individual electrochromic panes are characterized by first applying temporary bus bars and then coloring the electrochromic device. Visual defects such as halos are identified and then mitigated, for example, laser circumscribed to isolate them and remove the halo effect, which leaves smaller, less discernible, pinhole defects. As described above, conventionally, at least two, large, dedicated apparatus, are used to carry out identification and mitigation of visual defects. However, defects can form in the electrochromic devices after the devices leave the production facility due to, for example, the inherent stresses in electrochromic devices (e.g. see above) and/or stresses applied to the windows during normal use such as installation, pressure differential between interior and exterior space, impacts that do not break the window pane and the like. Conventionally, for electrochromic windows already installed in a vehicle or building, mitigating such defects would not be done, rather the unit would be replaced in the field. This can be very expensive. As well, mitigating defects in existing electrochromic windows in the field would greatly extend the usable lifetime of the windows. Thus embodiments described herein include portable apparatus for identifying and mitigating visual defects.

Portable Defect Mitigators

Embodiments described herein include apparatus and methods for identifying and mitigating visual defects in electrochromic or other devices where a visually discernible defect can be identified and mitigated as described herein. Such apparatus may be referred to herein as "defect mitigators," though their function includes components for both identifying and mitigating visual defects. In certain embodiments, apparatus for identifying and mitigating visual defects are portable. "Portable" in this context means that such apparatus can readily be moved and/or transported in order to identify and mitigate a visual defect in an electrochromic window or other device in the field, for example, an electrochromic window that is installed in a building, an automobile, and the like. That is, the apparatus can be, for example, carried by hand or otherwise manipulated by one or more users in order to position the apparatus proximate to an electrochromic window and carry out the functions of identifying a visual defect and mitigating the visual defect using the apparatus.

Portable apparatus for identifying and mitigating visual defects in electronic devices, such as those used in flat panel displays, photovoltaic windows and electrochromic windows, provide significant advantages over large, dedicated apparatus in a production facility setting. In particular, the portability of the apparatus allows for its use in the field, including on installed devices. Due to inherent stresses in electronic devices such as electrochromic windows and/or stresses applied to the devices, defects can form after the devices leave the production facility. This is a problem, especially for devices that are installed in a permanent fashion, such as an electrochromic window installed in a vehicle or building. Typically, when such visual defects arise in an electrochromic window, the window must be replaced. This can be costly, because electrochromic windows have associated wiring and related hardware. For example, recently, replacing four defective electrochromic windows in a prominent downtown London building was estimated to cost nearly € 1 million. As well, avoiding replacement by mitigating defects in existing electrochromic windows in the field would greatly extend their usable lifetime.

In certain embodiments, a portable apparatus will attach to the wall and/or window frame in order to carry out identification and mitigation of visual defects in an electrochromic window. In some embodiments, the portable apparatus will attach to the electrochromic window glass in order to identify and mitigate visual defects. This mode of attachment may be on a pane bearing an electrochromic device or a pane of an IGU that does not have an electrochromic device on it, e.g., defects are identified and mitigated on one pane, through another pane not having an electrochromic device. These and other aspects of embodiments are described in more detail below.

Some embodiments include an apparatus for mitigating a visual defect in an electronic device on a substrate, the apparatus including: a first mechanism configured to detect the visual defect; and a second mechanism configured to mitigate the visual defect. Apparatus described herein are particularly useful for identifying and mitigating visual defects where the electronic device on the substrate is an electrochromic window pane. In some embodiments, the first mechanism and second mechanisms are mounted on a movable stage, the movable stage configured to align the first and second mechanisms over all or substantially all of the viewable surface of the substrate. In one embodiment, the movable stage is an X-Y stage.

In some embodiments, the first mechanism includes an optical instrument. The optical instrument may be automated and thus include associated optical processing software. In one embodiment, the optical instrument includes at least one of a microscope, a camera, and a photo detector. For example, a microscope finds the center of a halo by measuring the relative intensity of light passing through the window (including any defects) and zeroing in on the maximum intensity region, which will typically be the center of the halo, and which also indicates the location of the defect to be remedied. Other types of detection mechanisms may rely on reflection or scattering of incident light (e.g. laser light, high intensity lamps, or ambient light). A microscope would typically be used during bright daylight hours when external radiation is impinging on the window undergoing defect detection; however a bright light or other source of visible energy, e.g. a laser source, may be used to illuminate the pane from the other side during darker hours of the day.

In some embodiments, a dark field illumination technique may be used to detect defects. In dark field illumination, sample contrast comes from light scattered by the sample. A dark field illumination technique can work well for defect detection when the defect causes a bump or other surface irregularity on the substrate; the dark field illumination technique can improve the contrast of such defects. For example, in the case of an electrochromic device disposed on a lite, the defect could include a particle with layers of the electrochromic device deposited over it, forming a raised bump in the electrochromic device.

Figure 4:
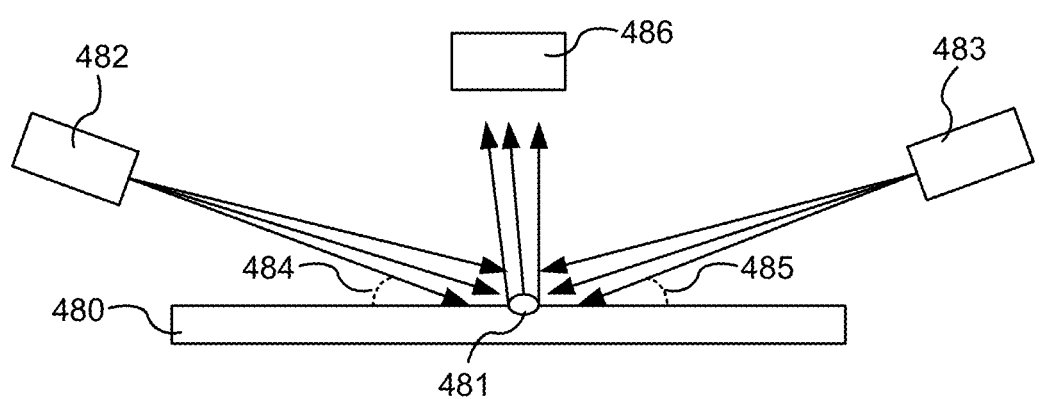
FIG. 4 depicts aspects of a dark field illumination technique.

As shown in FIG. 4, in dark field illumination, a substrate, 480, may include a particle, 481, creating an irregularity on the surface of substrate 480. Illumination sources, 482 and 483, may illuminate particle 481 at a small glancing or grazing angle (e.g., angles 484 and 485). An optical detector, 486, may detect light scattered from the irregularity on the surface of substrate 480. In some embodiments, dark field illumination employs a lens or other optical component to focus the scattered light onto optical detector 486.

Light incident upon the smooth regions of substrate 480 would reflect at wide reflection angles and would not be collected optical detector 486. In some embodiments, when multiple light sources or a circular light source (i.e., a light source configured to shine light from a perimeter of a circle onto a substrate) are used, the scattered light may form an image of the irregularity contour. In some embodiments, when a single or only a few light sources are used, the scattered light may give an indication of a surface irregularity, but may not form an image of the surface irregularity. In some embodiments, the first mechanism including components for dark field illumination may be on the same side of the substrate or lite as the second mechanism.

In some embodiments, the second mechanism includes at least one of a laser, a heat source, an induction coil, a microwave source, and a voltage source. If a laser is used, some thought must be given to ensuring the safety of those who might encounter the laser beam outside the building having a window where the remediation is being performed. In one embodiment, a laser having a very short focal length laser beam is used to mitigate defects so that any laser radiation passing outside the window will quickly diffuse over a wide area and become harmless. In one embodiment, laser energy is used to circumscribe a visual defect in such a manner so that it penetrates at least through the entire electrochromic device, including the electrochromic materials and both transparent conducting layers. The penetration may or may not pass through a diffusion barrier (if present) on the substrate. In another embodiment, mechanisms that allow detection and remediation after dark are used, so that there is a much lower likelihood of escaping laser radiation injuring citizens. In another embodiment, an opaque material is draped over the opposite side of the window upon which remediation is to take place. In another embodiment, the laser is tuned so that upon encountering the EC device and while mitigating the defect, the remaining energy of the laser beam is scattered or otherwise made diffuse so that any energy traveling past the window pane is harmless.

In some embodiments, a combination laser backstop/illumination device is used when the second mechanism includes a laser. A laser backstop/illumination device may be a battery powered device that is attached to the opposite side of the window from the laser during defect mitigation. For example, an illumination device may be useful in locating visual defects in an electrochromic device disposed on a window. The electrochromic device may be transitioned to a colored state, with the illumination device on a first side of the window and an optical instrument for detecting defects may be on a second side of the window. The illumination device, by shining light though pinholes or other visible defects in the electrochromic device, may make such defects more visible. In some embodiments, the illumination device includes a diffused light emitting diode (LED) backlight, a diffused halogen lamp, or other means of projecting light directly through the electrochromic device. For example, in some embodiments, the illumination device may include optics or components that use ambient light, including ambient sunlight, for a light source.

The illumination device is coupled with a laser backstop that may include a safety interlock. The illumination device would be protected against laser damage by an optical band-reject filter or other optical component that would block the wavelength of electromagnetic radiation of the laser.

In some embodiments, a laser backstop/illumination device and a laser include an active communication system. The communication system may be powered by a battery. For example, the communication system may include optical transceivers, inductive proximity detectors, or other means of wireless connection between the laser backstop/illumination device and the laser. When the communication system indicates that the laser backstop/illumination device and the laser are in close proximity to one another, on either side of the window, the laser backstop is in a position to block laser light and the laser is enabled. When the communication system indicates that the laser backstop/illumination device and the laser are in not close proximity to one another, the laser is not enabled. The default mode would be the laser not being enabled.

When using an apparatus for detecting and mitigating defects, with the apparatus including a laser backstop/illumination device, the apparatus could be operated by a single person or, for example, two or more people. For example, when one person is operating the apparatus, the user could attach the laser backstop/illumination device on an outside of a window on a building and then use the apparatus for mitigating defects. When two people are operating the apparatus, the people could work as a team; one person could be on the outside of the building and move the laser backstop/illumination device, and one person could be inside the building operating the apparatus.

In certain embodiments, apparatus described herein are portable. Generally, portable apparatus for identifying and mitigating defects should affix to or otherwise be held in position with respect to the window during operation. The associated mechanism for positioning may include, for example, a suction cup device that engages the frame or other structural feature around the window. In another mechanism, the apparatus is mounted on a rollable cart which has a vertically adjustable positioning mechanism for positioning the detection and remedying mechanisms during defect detection. This cart is wheeled or otherwise placed in position adjacent to a window undergoing defect detection and mitigation. Other positioning mechanisms are described below. In one embodiment, a portable defect mitigator is a handheld device having the features of a portable defect mitigator described herein.

Figure 5A:
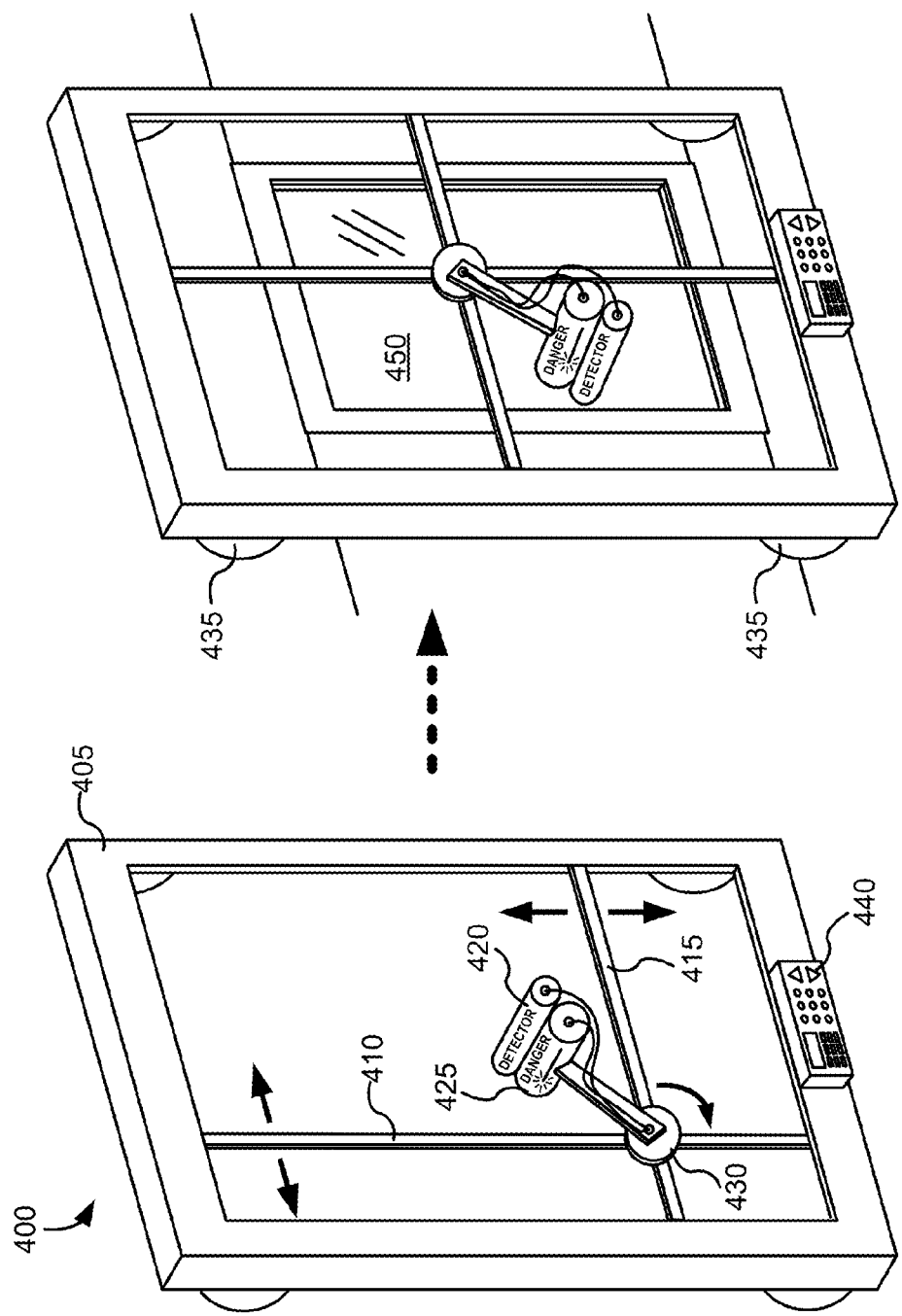
FIG. 5A depicts a perspective of an apparatus for identifying and remediating a visual defect.

Referring to FIG. 5A, a portable defect mitigator, 400, is depicted in perspective. Defect mitigator 400 has a frame, 405, which houses an X-Y stage including rails 410 and 415, along with other drive components (not shown), which allows base 430 to be positioned horizontally and vertically within frame 405. In this example, base 430 is rotatable about a central axis as depicted, and supports a defect detector, 420, such as an optical microscope, and a defect mitigator, 425, such as a laser. In this example, detector 420 and mitigator 425 are both supported on an arm which connects to base 430. In certain embodiments, apparatus described herein also include components for translating the defect detector and/or the defect mitigating component in the Z-direction, that is, toward and away from the window pane to be repaired. This may be necessary, e.g., when a laser or other focused beam mechanism is used to mitigate a defect in order to focus and/or position vertically within the stack, or attenuate the amount of energy applied to the electrochromic device.

Defect mitigator 400 also includes a controller, 440, in this example an onboard controller. In this example, electrical communication between controller 440 and detector 420 and mitigator 425 is hardwired as depicted. Base 430 has appropriate electrical connections, e.g., rotating electrical transfer components (commutator), which allow it to be rotatable while providing electrical communication between the components it supports and controller 440. Electrical communication between base 430 and controller 440 would also include, e.g., wires housed within rails 415 and 420 and appropriate electrical connections that allow the rails to translate while maintaining the electrical communication (the wires may also be outside the rails with appropriate measure to prevent entanglement with moving parts of the apparatus). In other embodiments wireless communication between the controller and defect detector and mitigator components is used. As one of ordinary skill in the art would appreciate, controller 440 has appropriate logic to send instructions to, and receive instructions from, the defect detector and mitigator components 420 and 425. Controller 440 may also contain memory, drivers for movement components, logic and the like.

In one embodiment, logic for controllers described herein includes: a first algorithm for scanning the electrochromic window pane with the first mechanism in order to detect the visual defect; and a second algorithm for positioning the second mechanism appropriately in order to mitigate the visual defect. In one embodiment, the first algorithm uses at least one of reflection, scattering and refraction, in order to identify a defect signature. The first algorithm may include instructions for scanning the entire surface of the viewable area of the electrochromic pane and assign coordinate data for each visual defect identified. The coordinate data may be stored in a memory and used by the controller to send instructions to the defect mitigator component. The coordinate system and window pane dimensions may be preprogrammed into the controller logic. In one embodiment, the logic includes instructions to scan the window to determine the window's viewable area and then establish a coordinate system based on the dimensions of the window, and e.g. the scanning device's limitations and/or operating parameters.

In certain embodiments, the second mechanism, the defect mitigator component, includes a laser and the second algorithm includes instructions for guiding the laser in order to circumscribe damage to the electrochromic device which is the underlying cause of the visual defect. In certain embodiments, all of the coordinates of the identified visual defects are stored in a memory and this information is used by controller logic to appropriately position the defect mitigator component in order to circumscribe each defect. The logic may include instructions for identifying all the defects prior to any mitigation, or, in some embodiments, each defect is identified and then mitigated, before moving on to identify more defects. In one case, the logic may include metrics used in automated identification of a defect, type of defect, and prioritization of the defects for mitigation. These metrics may be based on the size, shape, centroid location, and other characteristics of the defects.

As noted on the right hand side of FIG. 5A, apparatus 400 includes feet, 435, which attach frame 405 to, e.g., a wall in which an electrochromic window, 450, is installed. In this example, frame 405 of apparatus 400 is larger than window 450 so that the X-Y stage can be manipulated to position defect detector 420 and defect mitigator 425 over all areas of the glass of electrochromic window 450 in order to scan for and mitigate visual defects wherever they may be on the viewable area of the glass pane bearing the electrochromic device to be repaired (movement in the Z direction can be preset and defined once apparatus 400 is in place and/or in one embodiment there is a Z-positioning mechanism for 420 and/or 425). Feet 435 may be, e.g., suction cups, pressure-sensitive adhesive pads and the like. In certain embodiments, it may be necessary to attach apparatus 400 to the wall or window frame in a more secure fashion, e.g. via a temporary support such as one or more wall anchors, a z-bar or the like. Apparatus 400 may also include clamps, hooks or other components that allow it to hang over a window frame, support itself by clamping between bricks along a mortar line, and the like. In some embodiments, apparatus 400 is supported by legs, a tripod, a stand, a table, a cart or the like, whether or not it is also supported by a wall. In one embodiment, apparatus 400 is supported by one or more vertical supports, such as posts, where the posts are compressively positioned between the floor and ceiling, whether or not apparatus is also supported by a wall. One of ordinary skill in the art would appreciate that combinations of support mechanisms are within the scope of embodiments described herein. Polymeric suction cups, pressure-sensitive adhesive pads and other similar attachment mechanisms have the advantage of simplicity and dampening any vibrations that might otherwise travel between apparatus 400 and the surface to which it is affixed.

In one embodiment, the apparatus, e.g. as described in relation to FIG. 5A, does not affix to the wall or window, but rather frame 405 is movable along tracks or rails so that it can be moved, or via appropriate movement mechanisms. This is illustrated in FIG. 5B. A wall, 460, contains a number of windows in a linear arrangement, in this example a horizontal arrangement, but it could also be a vertical arrangement. A system of rails, 455, is established, e.g., affixed to wall 460, or e.g., compressed between adjoining walls to wall 460, or e.g. supported by stands at distal ends of the rails, etc. Rails 455 may have a circular cross section as depicted, or have rectangular, triangular or other geometric cross sections for added strength and decreased tendency to bend or otherwise deform while apparatus 400 is operating thereon. Apparatus 400, via appropriate movement mechanisms, "walks" along rails 400, scanning each window 450, identifying visual defects and mitigating them. This configuration has the advantage that an initial set up of the rail system will allow the apparatus to repair a number of windows, e.g. in a curtain wall, automatically without having to perform an alignment of apparatus 400 for each window individually. In one embodiment, apparatus 400 travels along rails or tracks 455 where contact with the rails is made via wheels having a polymeric component, e.g. polymeric wheels or hard wheels with a polymeric covering, such as nylon or silicone in order to minimize vibration during identification and mitigation. Although apparatus 400 in its entirety is not typically moving during identification and mitigation of defects, there may be vibration from the wall or other building component to which the rail system is attached.

As mentioned, in this example, apparatus 400 is larger than electrochromic window pane in window 450 for the described reasons. In one embodiment, the largest dimension of the apparatus is not substantially larger than the largest dimension of the electrochromic window pane. In one embodiment, the largest dimension of the apparatus is not more than about 20% larger than the largest dimension of the electrochromic window pane, in another embodiment, not more than about 10% larger than the largest dimension of the electrochromic window pane. In certain embodiments, described in more detail below, the largest dimension of the apparatus is the same or smaller than the largest dimension of the electrochromic window pane to be repaired. In one embodiment the apparatus is smaller than the electrochromic pane for which it is intended to repair. That is, the dimensions described above are meant to provide a metric for apparatus that use some form of attachment to a window and/or a wall, or that otherwise have a frame that is aligned in some way with the window to be repaired, for example, a frame containing an X-Y stage as described. As described above, in certain embodiments, apparatus are supported by a tripod, a cart, a table or the like, that does not affix to a window or wall.

In one embodiment, a handheld defect mitigator includes a defect detector, a defect mitigator and a controller, each as described herein, in a handheld configuration. A handheld defect mitigator may require two hands or only one hand to operate. Typically, but not necessarily, the handheld defect mitigator includes Z-direction positioning mechanism, which can be adjusted to particular needs, e.g., when mitigating through a non-EC pane of an IGU or directly through only the EC pane of the IGU. A handheld defect mitigator may have suction cups or adhesive pads to secure the apparatus to the glass at least during mitigation. In this context, a handheld defect mitigator may not use and/or include an automated X-Y positioning mechanism, but rather would rely on hand positioning at least to initially position the apparatus over a defect. After initial positioning, there may be some finer positioning hand operated mechanisms to move in the X-Y plane, such as thumbscrew adjustments and the like, to zero in on a defect. The optical instrument (e.g. a microscope) and mitigating mechanism (e.g. a laser) may be manually operated, or automatic once in position.

Figure 5C:
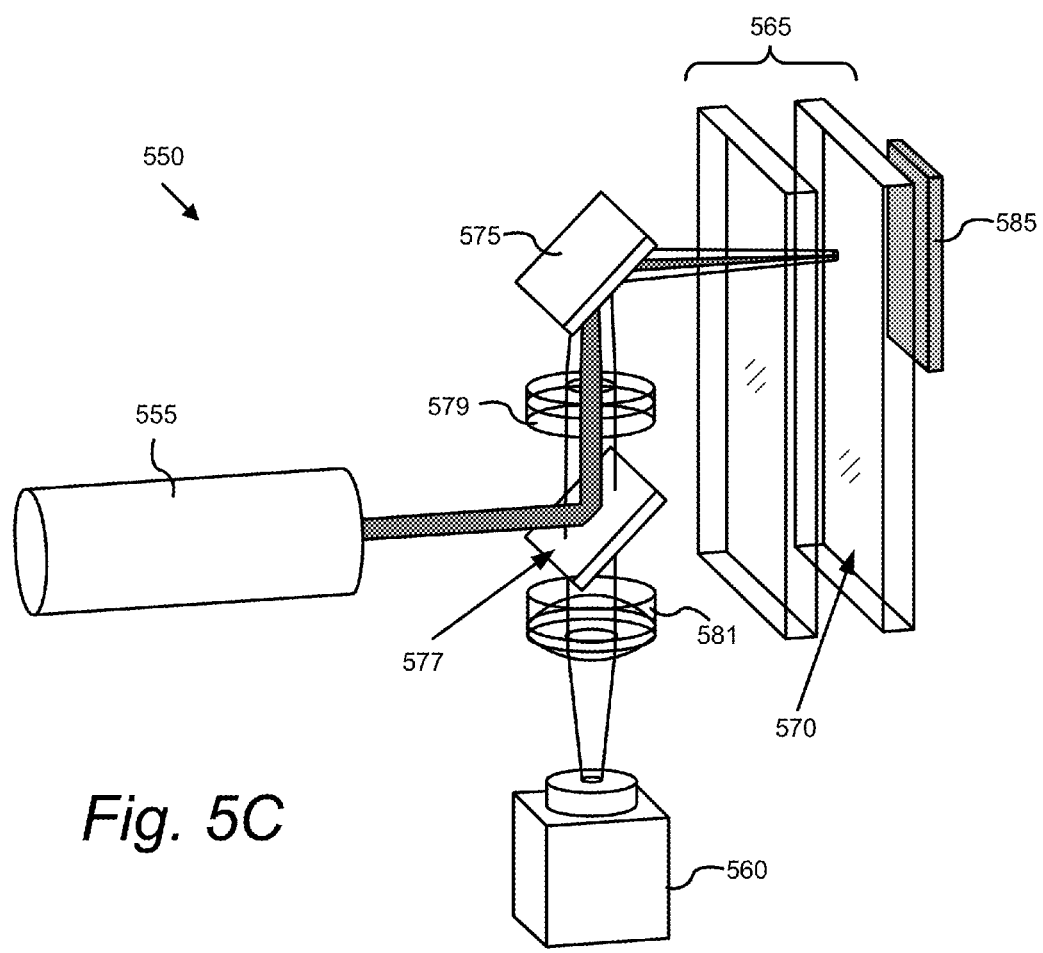
FIG. 5C depicts a coaxial optical path for laser and detection optics.

In some embodiments, a portable defect mitigator has an optical system with an optical detector, a laser and/or an illumination source sharing a coaxial optical path. FIG. 5C is a schematic drawing of components of a portable defect mitigator having an optical system 550 including a laser 555 and an optical detector 560. In this illustrated example, laser 555 and optical detector 560 having a co-axial optical path. In some cases, optical detector 560 includes a charge coupled device (CCD). Also shown in FIG. 5C is an IGU, 565, including two panes or lites, with an electrochromic device, for example, disposed on a surface, 570. The optical components of optical system 550 further include a first mirror, 575, a dichroic mirror, 577, and lenses, 579 and 581. Lens 579 may be an objective lens and lens 581 may be a condensing lens.

In operation, the electrochromic device disposed on surface 570 of IGU 565 may be transitioned to a colored state. An illumination device, 585, may be positioned to shine light though any defects in the electrochromic device. Light from illumination device 585 would reflect from first mirror 575 about 90 degrees, pass though lens 579, pass though dichroic mirror 577, pass though lens 581, and form an image of the defect that is detected by optical detector 560. Dichroic mirror 577 is specified such that the wavelength or wavelengths of light from illumination device 585 pass though the dichroic mirror. When optical detector 560 detects a defect, the defect may then be mitigated with laser 555.

In this example, light from laser 555 would reflect from dichroic mirror 577 about 90 degrees, pass though through lens 579, reflect from first mirror 575 about 90 degrees, and then impinge on surface 570. Dichroic mirror 577 is specified such that the wavelength of light from laser 555 is reflected by the dichroic mirror. Lens 579 focuses the light from laser 555 to a focal point on or near to surface 570 to concentrate the energy of the light to mitigate the defect.

Lens 579 may be adjusted to change the focal point of both laser 555 and optical detector 560. The focal plane of both the laser and the optical detector would be finely tuned to match by adjusting the position of lens 581. Thus, optical system 550 and other similar optical systems with a laser and an optical detector having a coaxial optical path allows the laser to be aimed at a defect and provides accurate alignment between the detection and mitigation processes.

In some embodiments, optical system 550 has a low mass. Because optical system may be mounted directly to a window, it is desirable to keep both the mass of the system and the moment perpendicular to the window low to prevent deflection of the window during operation of the system. For example, laser 555 may include a fiber coupled input with a low mass presenting a small perpendicular moment, with the laser source being mounted elsewhere (i.e., not on the window). Further, with one lens, lens 579, used to focus both laser 555 and optical detector 560, a single motor may be used to adjust the lens, reducing the mass of optical system 550. Optical system 550 may be positioned close to IGU 565 or other window while still keeping the majority of the mass along the vertical axis of the window.

One goal of the coaxial optics in optical system 550 is for the detection path and the laser path to "see" the defective surface as identically as possible. This facilitates the precise removal of the defect with minimal error in laser alignment. Even with coaxial optics, however, there may be alignment errors of the laser focal point associated with diffraction through the glass of the IGU, aberrations in a lens, glass warpage, the wavelength dependence of optics in the optical system, etc. These errors may create an offset between the center of the detection optics path and the center of the laser optics path, leading to laser alignment errors.

Figure 5D:
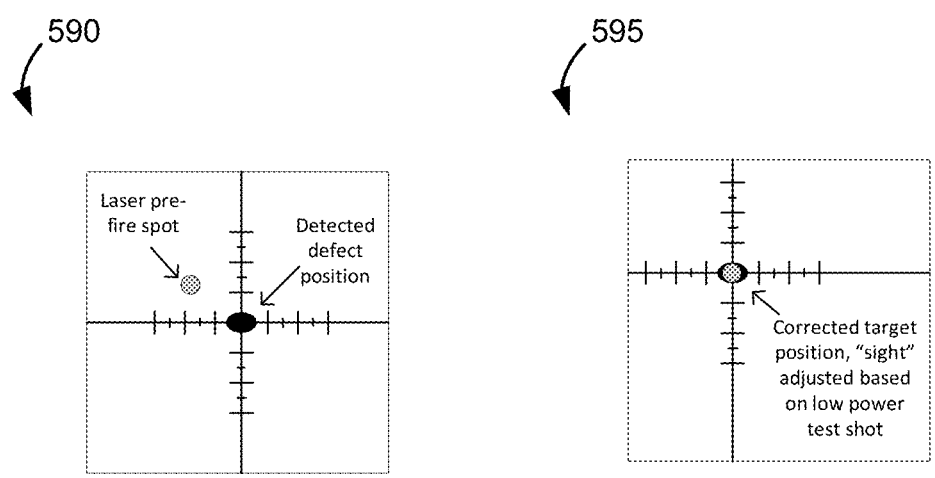
FIG. 5D depicts a pre-firing alignment process.

To remedy this, in some embodiments, optical system 550 may include a controller including program instructions for conducting a process. The process may include a low power firing sequence with the laser to ensure that the laser focal point is at the position of the detected defect. For example, in some embodiments, optical system 550 is aligned on a defect using the optical detector 560. Then, laser 555 emits light at a low power to create a visible spot of light on surface 570 which is reflected and imaged by optical detector 560. There may be an offset between where the defect is detected by optical detector 560 and the visible spot of light from laser 555 as shown in diagram 590 of FIG. 5D. The controller can then determine the exact positional offset between where the laser light is intended to intersect surface 570 during defect mitigation and where it actually will intersect surface 570. The alignments of optical system 550 is then adjusted to correct for any error in alignment prior to firing the laser at high power to mitigate the defect, as shown in diagram 595 of FIG. 5D.

Figure 6:
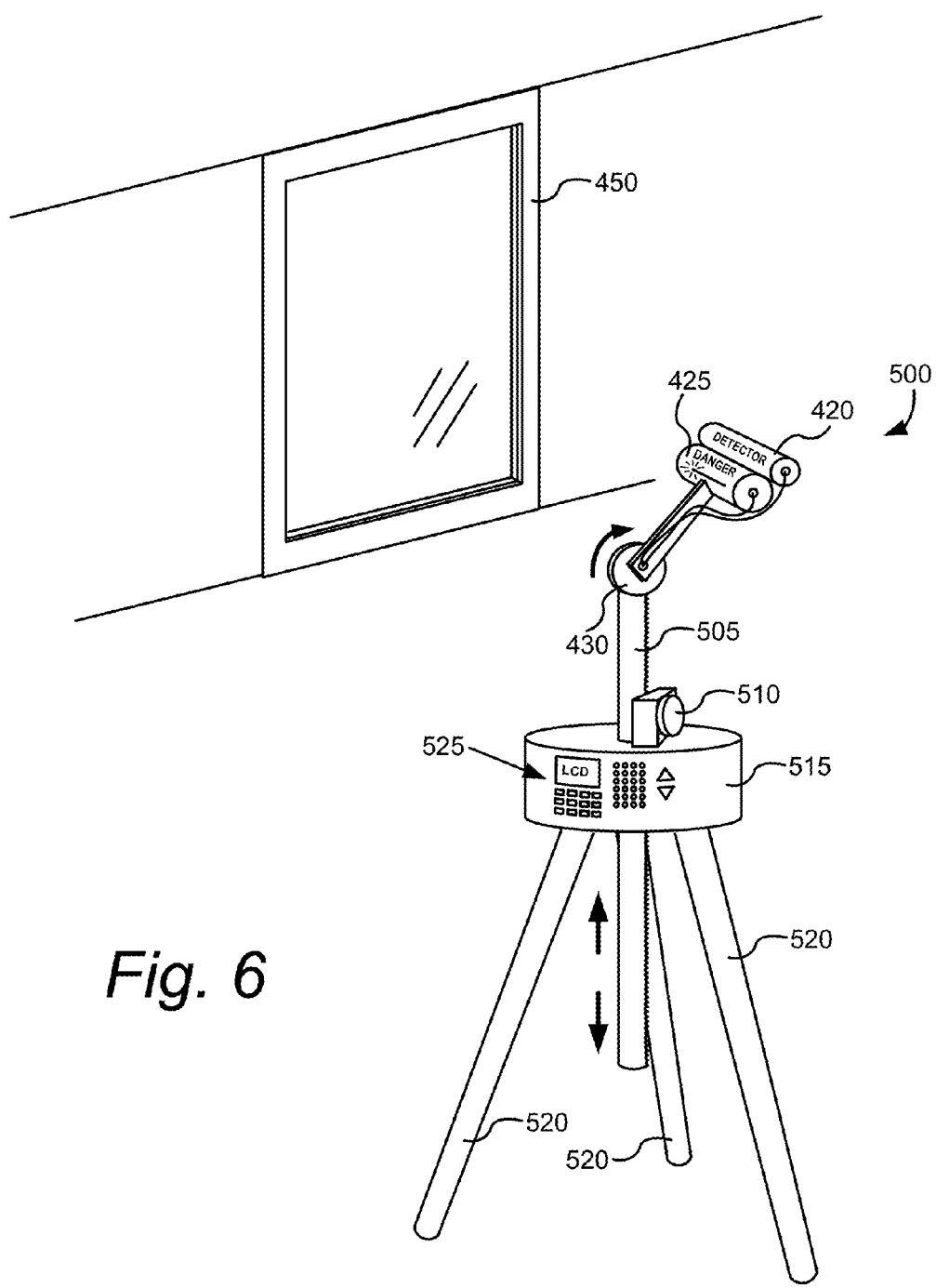
FIGS. 6 and 7 depict various aspects of apparatus for identifying and remediating a visual defect.

Referring to FIG. 6, a portable defect mitigator, 500, is depicted in perspective. Unlike defect mitigator 400, defect mitigator 500 does not have a frame, or an X-Y stage along with other drive components. Like apparatus 400, apparatus 500 does have a base 430 which is rotatable about a central axis as depicted, and supports a defect detector, 420, such as an optical microscope, and a defect mitigator, 425, such as a laser. In this example, detector 420 and mitigator 425 are both supported on an arm which connects to base 430. Base 430 is supported by a column, 505. Column 505 is movable along a vertical axis through an aperture in a body 515. Body 515 houses a controller 525, similar to controller 440 described above. In this example, via a drive mechanism, 510, column 505 is translated vertically, up or down through body 515, which is stationary and rests on legs 520. Controller 525 has a logic that performs the identification and mitigation of defects as described above in relation to apparatus 400; however, the movement algorithms for positioning detector 420 and mitigator 425 are different with respect to column 505 as compared to apparatus 400 which has an X-Y stage movement assembly (movement in the Z direction can be achieved manually in this case by appropriate placement of the tripod). In certain embodiments, which is true for all apparatus described herein, positioning, scanning and mitigation commands can be input manually, e.g., via a keypad or other input device on the controller. In some embodiments, once the apparatus is positioned and/or aligned, these functions are fully automated, that is, the apparatus automatically scans the window pane, identifies the visual defects according to programmed criteria and mitigates the visual defects. Apparatus 500 may also include components for translating the defect detector and/or the defect mitigating component in the Z-direction, that is, toward and away from the window pane to be repaired as described in relation to apparatus 400.

During operation, apparatus 500 is positioned and aligned appropriately in front of window 450 so that detector 420 and mitigator 425 can scan and identify and mitigate visual defects across the entire viewable area of electrochromic window 450. Apparatus 500 has the advantage of being compact relative to, e.g., an apparatus having a large frame and X-Y stage, e.g., legs 520 may be telescopic and foldable when not in use.

In some embodiments, the largest dimension of the apparatus is smaller than the largest dimension of the electrochromic window pane and the apparatus mounts to the electrochromic window that includes the electrochromic pane during operation. In one embodiment, the apparatus mounts to the window pane (glass) itself, without having to touch the window frame or wall. In this embodiment, the apparatus may attach to the window via at least one of a suction cup and a pressure-sensitive adhesive. This may include a handheld defect mitigator as described herein (e.g. an apparatus not having an X-Y stage positioning components).

Figure 7:
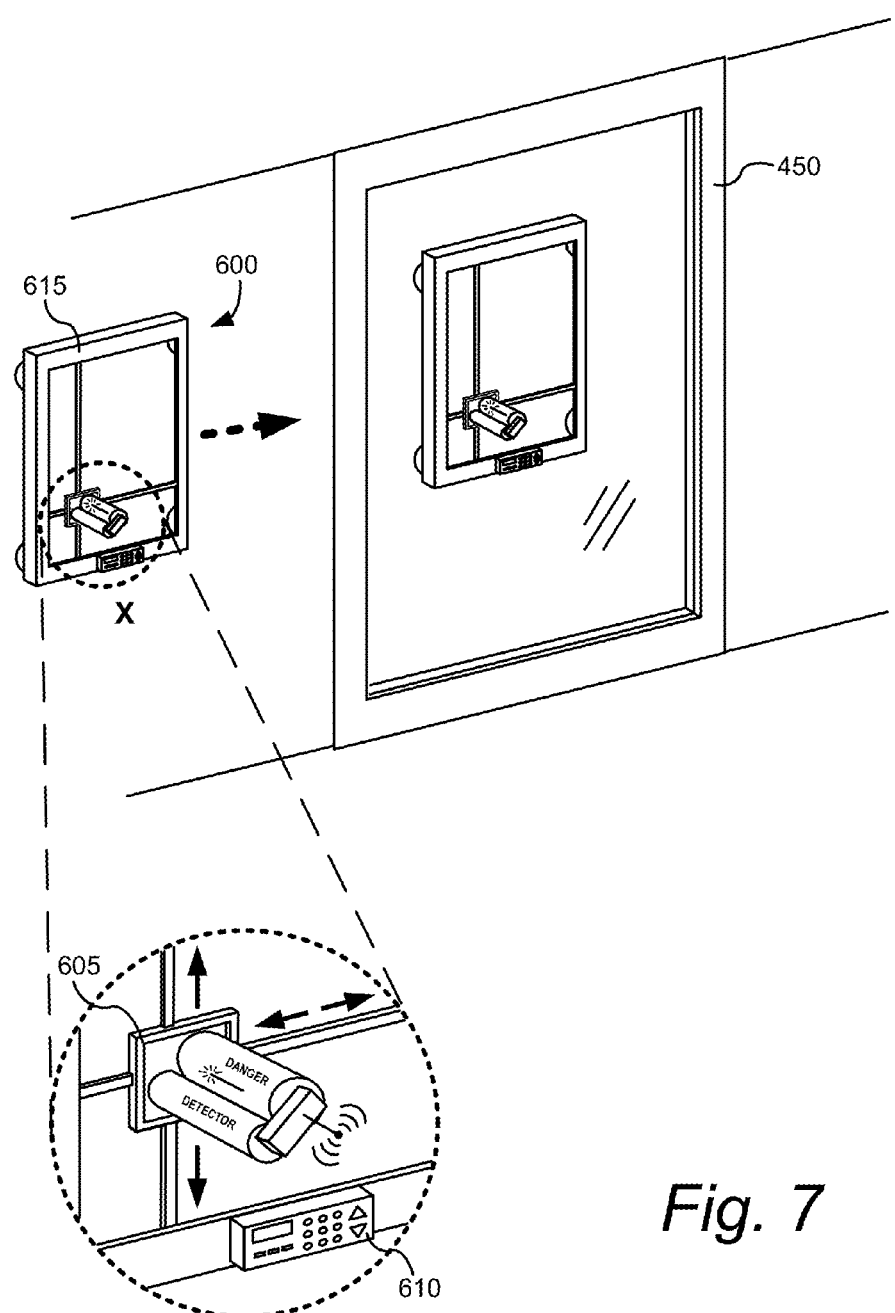

Referring to FIG. 7, a portable defect mitigator, 600, is depicted in perspective. Like defect mitigator 400, defect mitigator 600 has a frame, and an X-Y stage along with other drive components. Also, like apparatus 400, apparatus 600 has a base 605; however base 605 is non-rotatable. In this example, base 605 is a frame through which the detector component can scan the pane of window 450 to locate and identify visual defects and the mitigator component can mitigate the defects. The X-Y stage in apparatus 600 moves base 605 about the area inside the frame 615 of apparatus 600. Although apparatus 600 cannot identify and mitigate defects over the entire area of window 450 while in a single position, it has the advantage of being small and more easily ported to the jobsite. In some instances, a customer might have only a few halo effects on a window, or windows, and such an apparatus would be more easily positioned over the halo in question for remediation efforts. In this example, referring to expanded portion X in FIG. 7, wireless communication is used between detector/mitigator components and controller 610. One embodiment is any apparatus described herein, e.g. apparatus 400 or 500, further including wireless communication between the detector and/or mitigator and the controller. One of ordinary skill in the art would appreciate that such apparatus would include appropriate wireless antennae, receivers and transmitters. The controller need not be affixed to the frame or other component of the apparatus; rather it can be in the form of a remote control device.

One embodiment is a method of mitigating a visual defect in an electrochromic window installed in a building or an automobile, the method including: (a) identifying the visual defect in the electrochromic window; and (b) mitigating the visual defect using at least one of a laser, a heat source, an induction coil, a microwave source and a voltage source. In one embodiment, the electrochromic window is colored prior to (a) or as part of the identification process. Apparatus as described herein are particularly useful for implementing methods described herein.

Figure 8A:
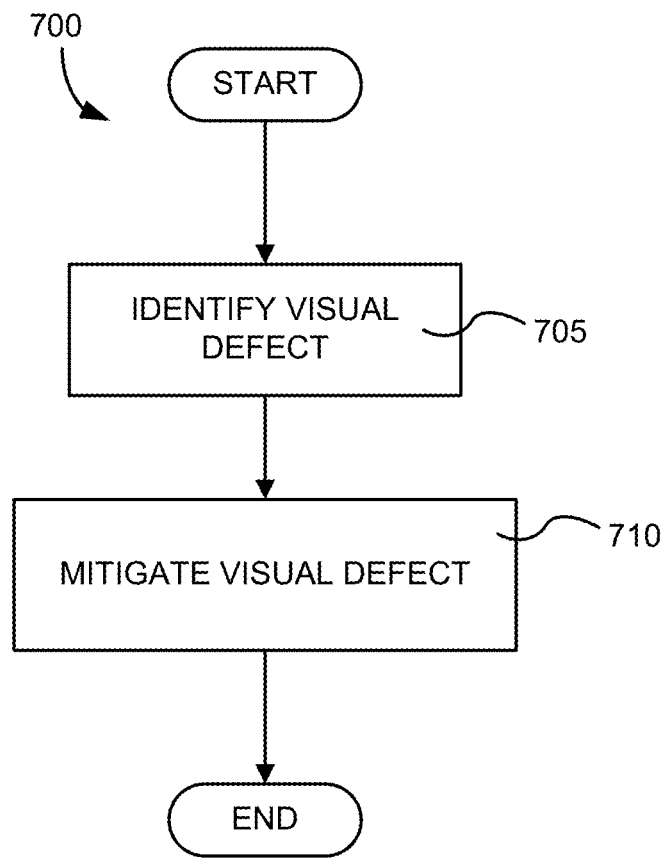
FIGS. 8A-8C depict aspects of a process flow.
Figure 8B:
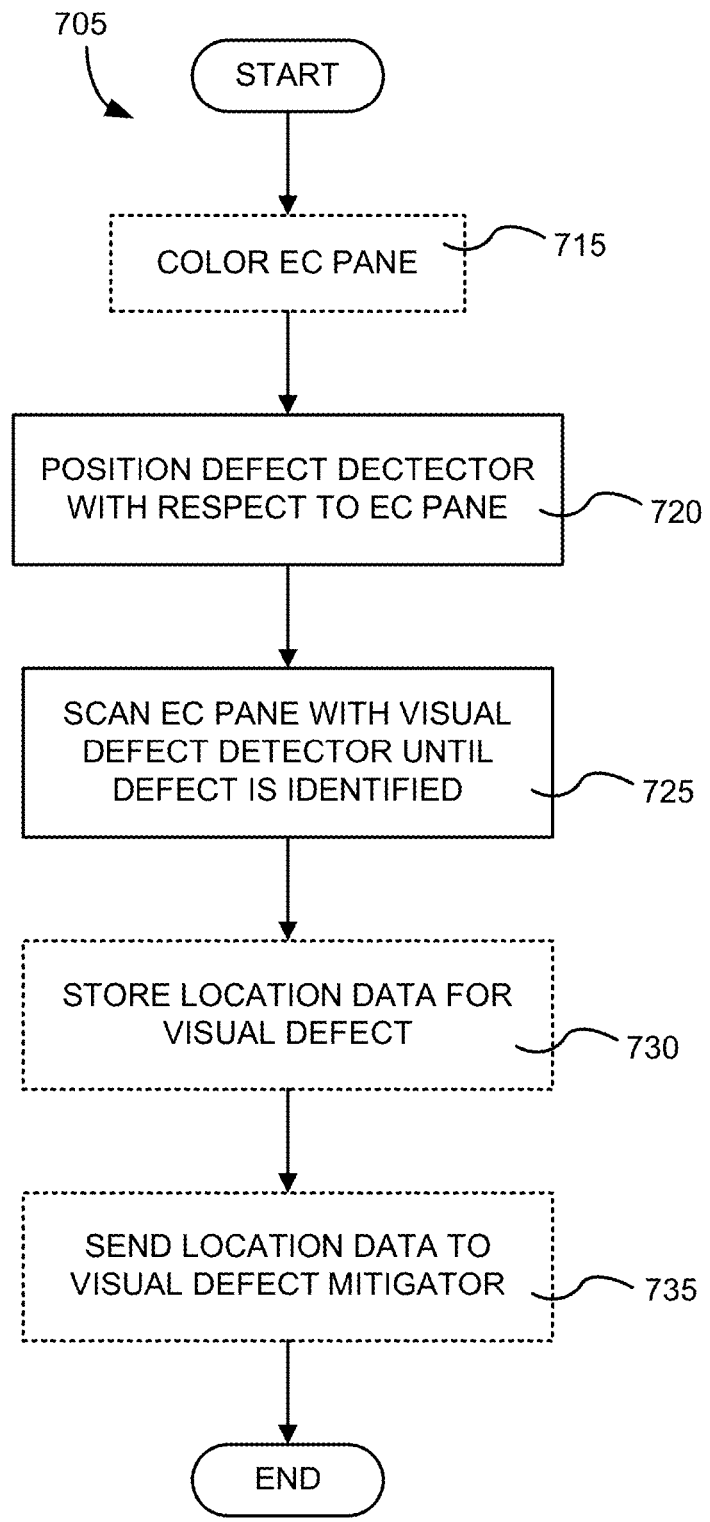

FIG. 8A depicts aspects of a method, 700, which begins with identifying a visual defect, see 705. As described, apparatus described herein, once positioned appropriately, may scan an electrochromic pane in order to locate and identify visual defects. FIG. 8B outlines an embodiment of process flow 705. First the electrochromic pane is colored, see 715. The defect detector is then positioned with respect to the pane, see 720. Steps 715 and 720 may be done in reverse order or simultaneously. If the pane is already colored, then step 715 is optional. Next, the electrochromic pane is scanned, see 725. As described above, this may be accomplished with controller logic having instructions for particular scanning algorithms. Optionally, the coordinates of the visual defect may be stored in a memory, e.g., part of the controller, see 730. Next, e.g. when a controller logic is used, the coordinates of the visual defect may be communicated to the defect mitigator mechanism, see 735. Then the identification operations end.

Figure 8C:
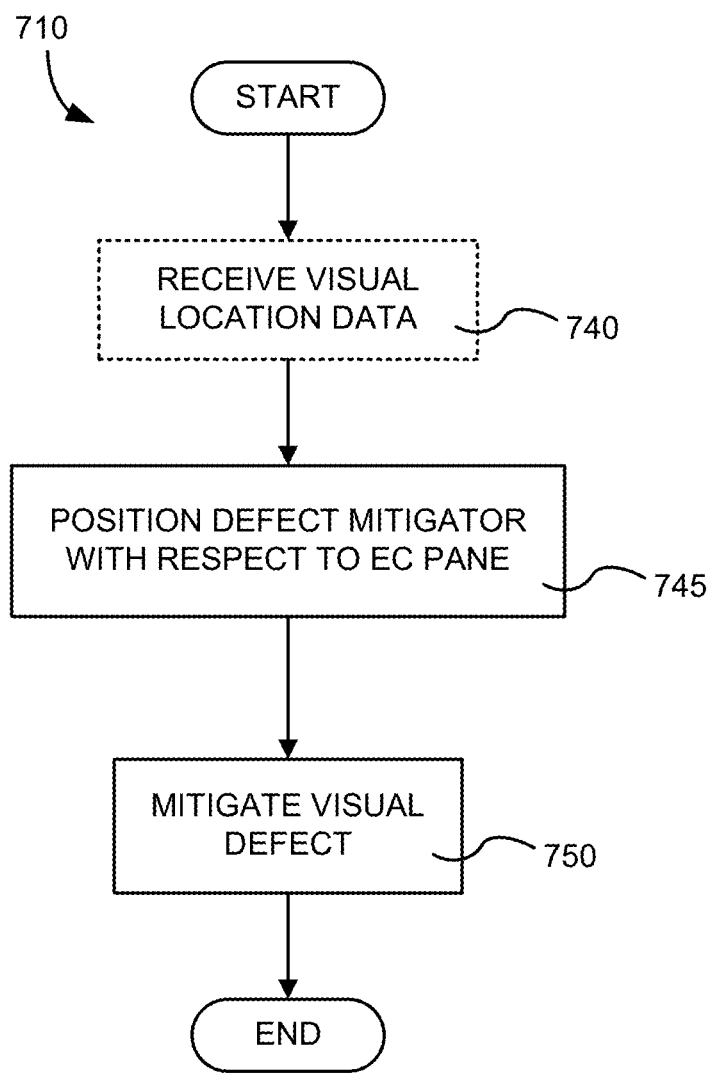

Referring back to FIG. 8A, after the visual defect is identified, it is then mitigated using the mitigation mechanism, see 710. FIG. 8C outlines an embodiment of process flow 710. Assuming the visual defect's coordinates were sent to, e.g. a mitigation mechanism, the data is received by the mitigation mechanism, see 740. The defect mitigation mechanism is then positioned with respect to the electrochromic pane appropriately to mitigate the defect, e.g., circumscribe the defect with a laser, see 745. Once positioned, the defect is mitigated, see 750. Then the process flow ends.

In certain embodiments, a laser is used to mitigate a defect. Electrochromic windows may have an EC device on the inner surface of the outer (on the outside of a building) pane of glass, while the inner pane does not have an associated EC device. Lasers are particularly useful for mitigation because they can be tuned so that the laser beam is passed through the inside pane of glass in order to mitigate a defect in the EC device on the outer pane (e.g. inside a window unit, two panes with a separator between them, e.g. a simple IGU). One embodiment is a method of mitigating a visual defect in an electrochromic device on a glazing that is part of a window unit, the method including: (a) identifying the visual defect in the electrochromic device; and (b) mitigating the visual defect using a laser. In one embodiment, the electrochromic device is colored prior to (a) or as part of the identification process. In one embodiment, the window unit is an IGU having a first and a second pane (glazing), where the first pane bears an electrochromic device and the second pane does not have an electrochromic device thereon. In one embodiment, the laser energy is passed through the second pane and a defect in the electrochromic device on the first pane is mitigated. In one embodiment, the laser energy is passed through the first pane and a defect in the electrochromic device on the first pane is mitigated.

Mitigating defects using laser energy that passes through a pane of an IGU, through the volume of the IGU and ablates an electrochromic device on an opposing pane is different than mitigating defects in an electrochromic device sealed in a laminated structure, e.g., as described in U.S. Pat. No. 7,531,101. For example, in such laminated structures, there is necessarily an interlayer material such as a thermoplastic polymer material that binds the substrates together. This material can affect the ability to ablate an electrochromic device if the laser energy must pass through the interlayer material, for example the interlayer material may be an absorber of the laser energy. For example PVB and polyurethane interlayer materials may absorb certain wavelengths of energy. Also, due to the distance between the panes of an IGU in the volume of the IGU, the focal distance, power and choice of laser may vary considerably.

In certain embodiments, apparatus and methods herein are used to identify and mitigate defects in electrochromic windows that have at least one EC device on both the inner and the outer pane of the IGU. Electrochromic windows having this architecture are described in U.S. patent application Ser. No. 12/851,514, filed Aug. 5, 2010, and entitled, "Multi-pane Electrochromic Windows," by Friedman et al., which is incorporated by reference herein in its entirety.

When defects in such windows are mitigated, for example a window having one EC device on each pane of an IGU, identification and mitigation of defects are typically, but not necessarily, carried out while one pane's EC device is bleached so that the other pane's EC device can be colored and any defects identified and mitigated. Once one pane's defects are mitigated, the EC device on the processed pane is bleached and the other pane is colored in order to carry out identification and mitigation operations on that pane. Identification and mitigation may be carried out from a single side of the window, for example the interior of the building, because the inner pane can be bleached and the laser tuned to pass through the bleached pane and mitigate the outer pane's colored EC device.

Dynamic Autofocusing System

Although windows are substantially rigid, they may have some degree of flex under certain circumstances. For example, an electrochromic window, particularly a large electrochromic window, may flex somewhat while being installed and when subject to external forces such as wind. If an electrochromic window flexes during the course of defect imaging and mitigation, the maximum flux of radiant energy at the focal point of the laser may not remain aligned to the targeted portion of the window. Typically, the focal point should be targeted to a position at or very near the surface of the electrochromic device near the defect. If the focal point of the laser does not remain aligned to the targeted location, defect mitigation (and/or imaging) may become less effective. Dynamic autofocus systems disclosed herein can be employed by the defect mitigator to help ensure that the focal point of the laser remains consistently aligned to the targeted location even while the window may be flexing or otherwise moving over the course of the imaging and mitigation process.

One way that a dynamic autofocus system can address this challenge is by automatically adjusting the position of a lens to focus the laser light to the targeted location as the window flexes or otherwise moves during defect imaging and/or mitigation. For example, the lens can be automatically adjusted to maintain the lens at a particular separation distance D (e.g., a distance at about a focal length of the lens from the surface) from the targeted location or maintain the lens within a range of distances from the particular separation distance D from the target location. The target location is typically at a surface of the electrochromic device having the defect.

In some cases, these automatic adjustments can be accomplished with a suitably fast feedback/control system. This system includes a processor (e.g., microprocessor) that sends signals to a lens positioning mechanism capable of moving the lens in response to certain detected movements of the surface of the electrochromic device or other suitable portion of the window. The processor is in communication with a detecting mechanism that detects these movements.

During defect mitigation, the processor may receive signals with data from the detecting mechanism. The data may include the location of the surface or other portion of the window at the time of detection. The processor may determine the current separation distance D and/or the movement of the window since the last sampling time. The processor may then determine whether the current separation distance D (or movement) at the time of detection requires that the lens move to correct the position of the focal point at the targeted portion of the window. For example, the processor may determine whether the difference between the current separation distance D and the focal length of the lens is more than certain percentage difference (e.g., 0.001%, 0.01%, 0.1%, 1%, 2%, etc.) to determine whether the difference is within an acceptable range. As another example, the processor may determine whether the difference between the current separation distance D and the focal length of the lens is more than a maximum difference (e.g., 0.01 mm, 0.1 mm, 0.2 mm, etc.) to determine whether it is within an acceptable range. If the surface has moved out of the acceptable range, the processor determines a new location of the lens with a separation distance D within the acceptable range. For example, the new location may be a distance (from the current location) equal to the measured separation distance D less the focal length. The processor then sends a control signal to the lens positioning mechanism 1020 to move the lens to the new location. Dynamically adjusting the lens to maintain the separation distance D within this acceptable range, keeps the laser in focus substantially locating the focal point at the target location for mitigating the defect. The acceptable range may be related to the size and centroid location of the focal point of the laser being employed.

In some instances, there may be a significant lag time between the sample time at which the separation distance is measured and the time at which the lens has moved to the new location. To lessen the impact of such a lag time, certain embodiments of the portable defect mitigator may include a processor that can predict a separation distance D at a future time based on measurements from the detection mechanism (e.g., triangulation sensor) taken at one or more sample times. In these cases, the detection mechanism may determine the separation distance D and a rate of change of the separation distance D at a sample time. The processor can determine the future separation distance D at a future time based on the separation distance D and rate of change measured at the sample time. If the surface is predicted to move out of the acceptable range by the future time, the processor can determine a new location of the lens with a separation distance D within the acceptable range that is appropriate for the future time. The processor then sends a control signal to the lens positioning mechanism 1020 to move the lens to the new location and the lens moves to the new location by the future time.

Figure 9:
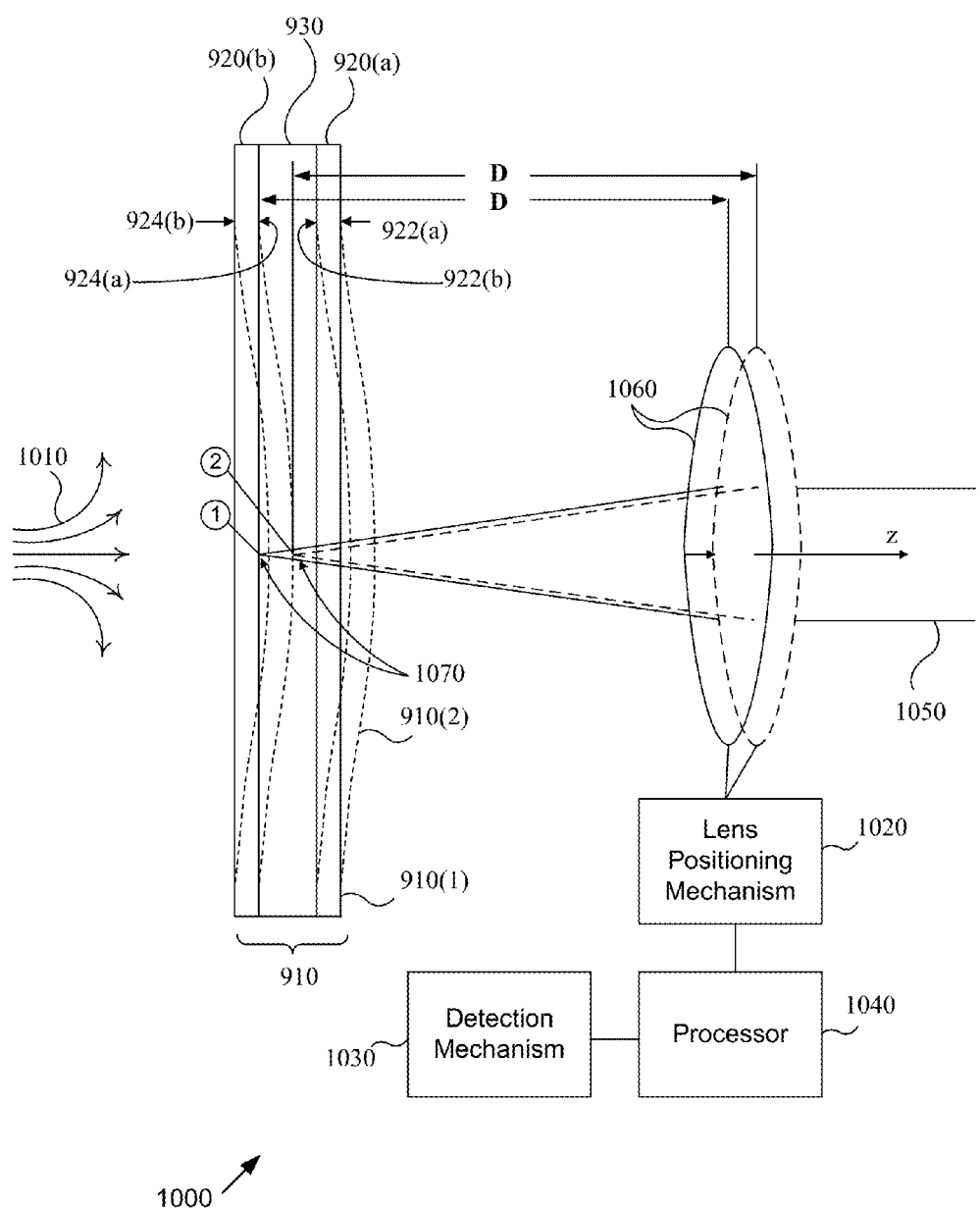
FIG. 9 is a schematic diagram of a dynamic autofocus system in a portable defect mitigator, according to embodiments.

FIG. 9 is a schematic illustration of a mitigation process using a dynamic autofocus system 1000, according to embodiments. In this example, the mitigation process is being performed on a window unit 910 having a first electrochromic window pane 920(*a*), a second electrochromic window pane 920(*b*), and a sealing separator 930 between the first and second panes 920(*a*), 920(*b*). The first electrochromic window pane 920(*a*) has a first surface 922(*a*) and a second surface 922(*b*). The second electrochromic window pane 920(*b*) has a first surface 924(*a*) and a second surface 924(*b*). Each of the electrochromic window panes 920(*a*), 920(*b*) includes an electrochromic device on one side or both sides of a substantially transparent sheet (e.g., glass sheet). The illustrated window unit 910 may be part of an IGU. Although an electrochromic window is shown in FIG. 9 and other illustrated embodiments, any window with an optically switchable device can be used.

In FIG. 9, a wind force 1010 is impinging the second surface 924(*b*) of the second electrochromic window pane 920(*b*). The wind force 1010 is causing the window unit 910 to bend and bow inward at the center portion. The illustration shows the window unit 910 at two instances before flexing 910(1) (at time $t_0$) and after flexing 910(2) (at time $t_1$ occurring during the mitigation process). Although a wind force is used in embodiments, other forces may cause deformation of the window panes. For example, building vibrations from a train or construction may cause deformation.

The illustrated dynamic autofocus system 1000 includes a lens positioning mechanism 1020, a detection mechanism 1030, and a processor 1040 in communication with the lens positioning mechanism 1020 and the detection mechanism 1030. A laser (not shown) provides a collimated laser beam 1050 used to mitigate the defect. The lens positioning mechanism 1020 is in communication with a lens 1060 used to focus the collimated laser beam 1050 to a focal point 1070. The focal point 100 is located at or near a target location for mitigating the defect. In this example, the target location is at the second surface 924(*b*) of the second electrochromic pane 920(*b*). In other embodiments, the target location may be at other locations of the window unit 910.

During the mitigation process illustrated in FIG. 9, the detection mechanism 1030 measures the location of the second surface 924(*b*) and/or another surface (e.g., 924(*a*), 922(*a*), 922(*b*)) at different sampling times, $t_1, t_2, \ldots t_n$. Alternatively, the detection mechanism 1030 may measure the location of the target portion. At each sampling time, the detection mechanism 1030 sends signals to the processor 1040 with the location data. In the illustration, the detection mechanism 1030 measures the location of the second surface 924(*b*) near the defect at time $t_1$ and sends signals with data to the processor 1040 with the location at time $t_1$. The processor 1040 sends control signals to the lens positioning mechanism 1020 to move the lens 1060 from a first position to a second position along a z-axis located along the centerline axis of the collimated laser beam 1050. This movement keeps the separation distance D between the target location at the second surface 924(*b*) and the lens 1060 to a constant value equal to the focal length to keep the focal point 942 at the second surface 924(*b*) during the mitigation process. In other examples, the detection mechanism 1030 may detect a location on multiple surfaces or other surfaces of the window. In some cases, the surface detected by the detection mechanism 1030 may correspond to the closest surface to the defect.

As explained, the maximum flux of radiant energy (at the focal point) should be located at the targeted portion of the electrochromic device to be mitigated. Another possible way to address this challenge involves using a laser beam that is relatively insensitive to changes in distance D. Such a beam would have a relatively long focal point (i.e., long in the direction of beam propagation). The focal point length would be great enough to permit mitigation over the full range of variations in D encountered during movement of the electrochromic window. The length of the beam that provides a relatively invariant radiant energy flux (the focal region) is sometimes referred to as the "depth of focus" of the beam. Achieving a depth of focus of greater than about ±500 μm (i.e., greater than 1000 μm total depth) is typically problematic. A depth of focus this great may make the spot area of the laser beam too great to effectively scribe. Further, the separation distance of the laser optics (e.g., the condensing lens) from the tool may be too great. In some embodiments, suitable depth of focus ranges are about ±100 μm or less, or about ±50 μm or less. Therefore, the depth of focus of a laser is typically too short to allow the system to operate without adjusting the lens position in order to maintain a separation of D.

Various possible focus control mechanisms that can be employed as a detection mechanism 1030 in the dynamic autofocus system to ensure that the focus of the laser remains focused during mitigation at the proper height (e.g., z-position in FIG. 9) through the thickness of the window. One type of design employs confocal detection and patterning beams. A detection beam is used to determine the distance between the surface of interest and a frame of reference. Generally a confocal system is one where the patterning and detection beams (or any other two beams) share the same focal point. They may, in some embodiments, share the same optics.

Figure 10:
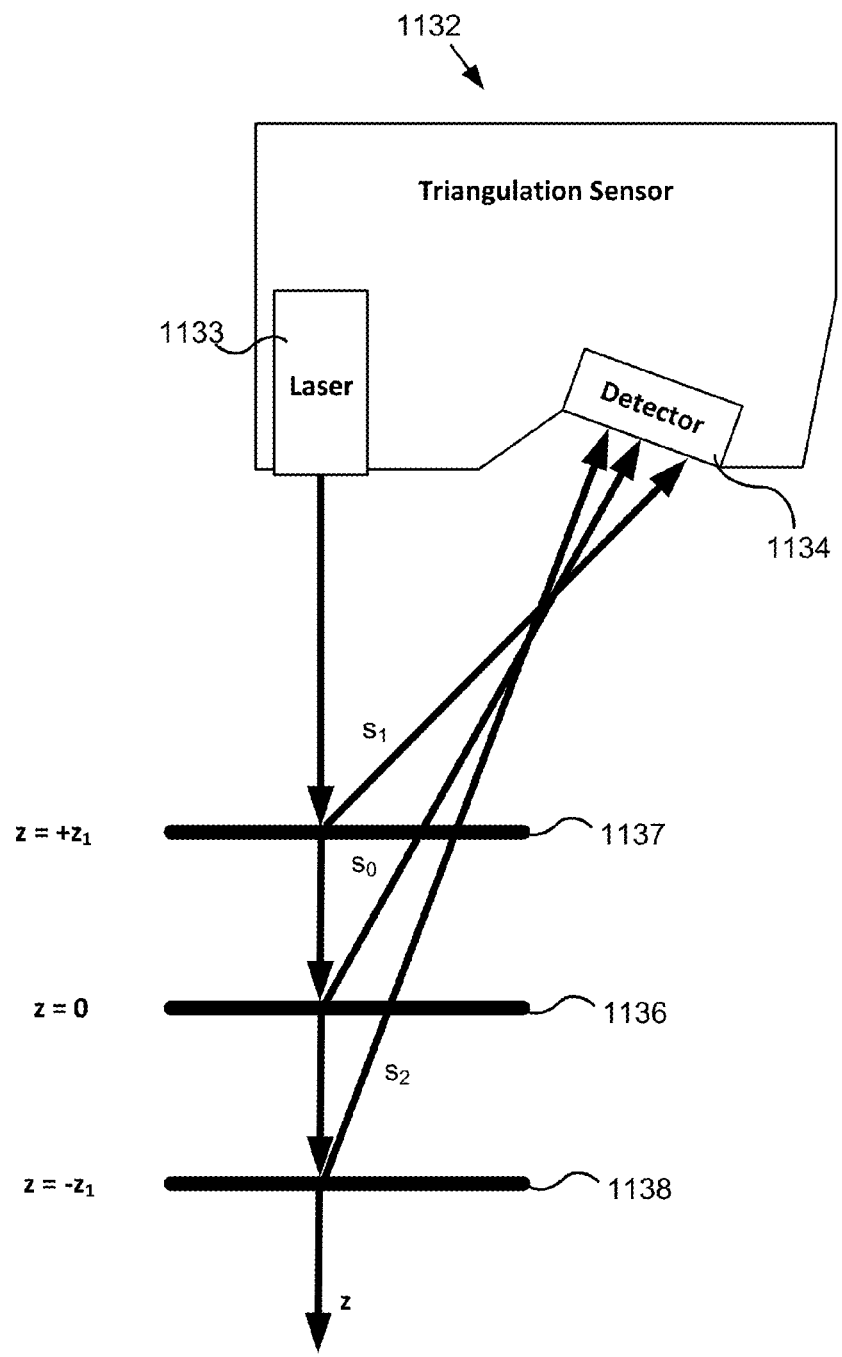
FIG. 10 is a schematic diagram of a triangulation sensor of a dynamic autofocus system, according to embodiments.

Another type mechanism that may be used as a detection mechanism 1030 in the dynamic autofocus system 1000 is a triangulation sensor. Some examples of triangulation sensors that can be employed as detection mechanisms 1030 can be found in U.S. patent application Ser. No. 13/436,387, filed on Mar. 30, 2012, which is hereby incorporated by reference in its entirety. FIG. 10 illustrates an example of a triangulation sensor 1132 that can be used as a detection mechanism in the dynamic autofocus system, according to embodiments. The triangulation sensor 1132 includes a laser 1133 and a detector 1134. In some embodiments, laser 1133 may be a lower power laser that does not scribe or melt a substrate, but is reflected from the substrate. In many cases, the laser 1133 is a blue laser. In some cases, the detector 1134 may be a charge coupled device (CCD). Detector 1134 is positioned to face a direction at a fixed angle from laser beam path. The triangulation sensor 1132 may be mounted to the same block that holds the focal lens.

In operation, triangulation sensor 1132 projects a laser beam from laser 1133 onto a surface of an electrochromic window. The laser beam is reflected from the surface and onto different regions of detector 1134. From the region of detector 1134 that the laser beam is reflected onto, the distance of the surface of the electrochromic window from triangulation sensor 1132 can be determined. For example, as the electrochromic window moves in the z-direction along a z-axis at the centerline of the laser beam propagation, the lateral movement as detected by detector 1134 is converted to a distance reading between triangulation sensor 1132 and the surface of the electrochromic window.

Triangulation sensor 1132 can determine a distance of a surface of the electrochromic window from triangulation sensor 1132 and or the distance of the surface of the electrochromic window to the focal lens of the dynamic autofocus system 1000. For example, triangulation sensor 1132 may determine a nominal distance $s_0$ from the surface at a position 1136 at height of z=0 where the electrochromic window is in a baseline state (not flexing or otherwise moving). As another example, triangulation sensor 1132 may determine a distance $s_1$ from the surface at a position 1137 at height of z=+$z_1$ where the electrochromic window flexed and the position has moved in the positive z-direction by $z_1$. As another example, triangulation sensor 1132 may determine a distance $s_2$ from the surface at a position 1138 at height of z=−$z_1$ where the electrochromic window flexed and the position has moved in the negative z-direction by $z_1$. In some cases, the triangulation sensor 1132 may be restricted to measuring distances between a minimum distance and a maximum distance. In these cases, the triangulation sensor 1132 may be set or calibrated based on the nominal distance.

In one embodiment, the dynamic autofocus system adjusts the focus lens 1060 such that the beam emitted from the laser impinges a second side of the second side of the electrochromic pane and is focused at the interface of the first side of the electrochromic pane and the electrochromic device, as determined by the triangulation-based distance sensor 1132. For example, a feedback loop may be implemented such that the focus lens 1060 adjusts rapidly based on the determination by the triangulation-based distance sensor. In some embodiments, a signal from the triangulation-based distance sensor 1132 may be an analog signal which may aid in enabling the rapid adjustment of the focus lens 1060.

Examples of Handheld Portable Defect Mitigators

In some embodiments, the portable defect mitigator may be a handheld design that can be affixed directly to the surface of the window during defect imaging and mitigation. These handheld defect mitigators may include one of the optical systems disclosed herein. Optical systems with components in a compact arrangement that may be particularly suitable for such a handheld design are shown in FIGS. 11A, 11B, and 12.

Figure 11A:
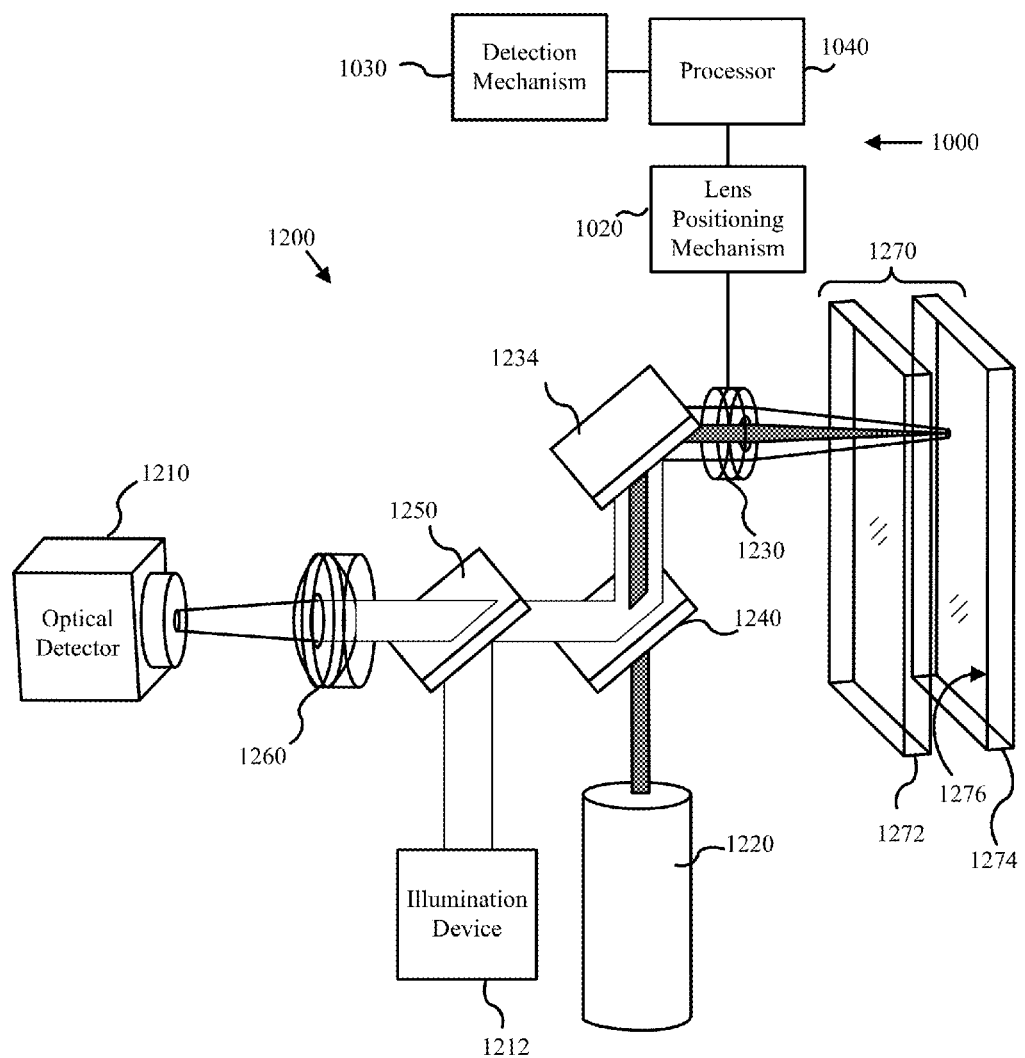
FIG. 11A is a schematic diagram of an optical system in a compact arrangement having a mirror at a nominal position, according to embodiments.
Figure 11B:
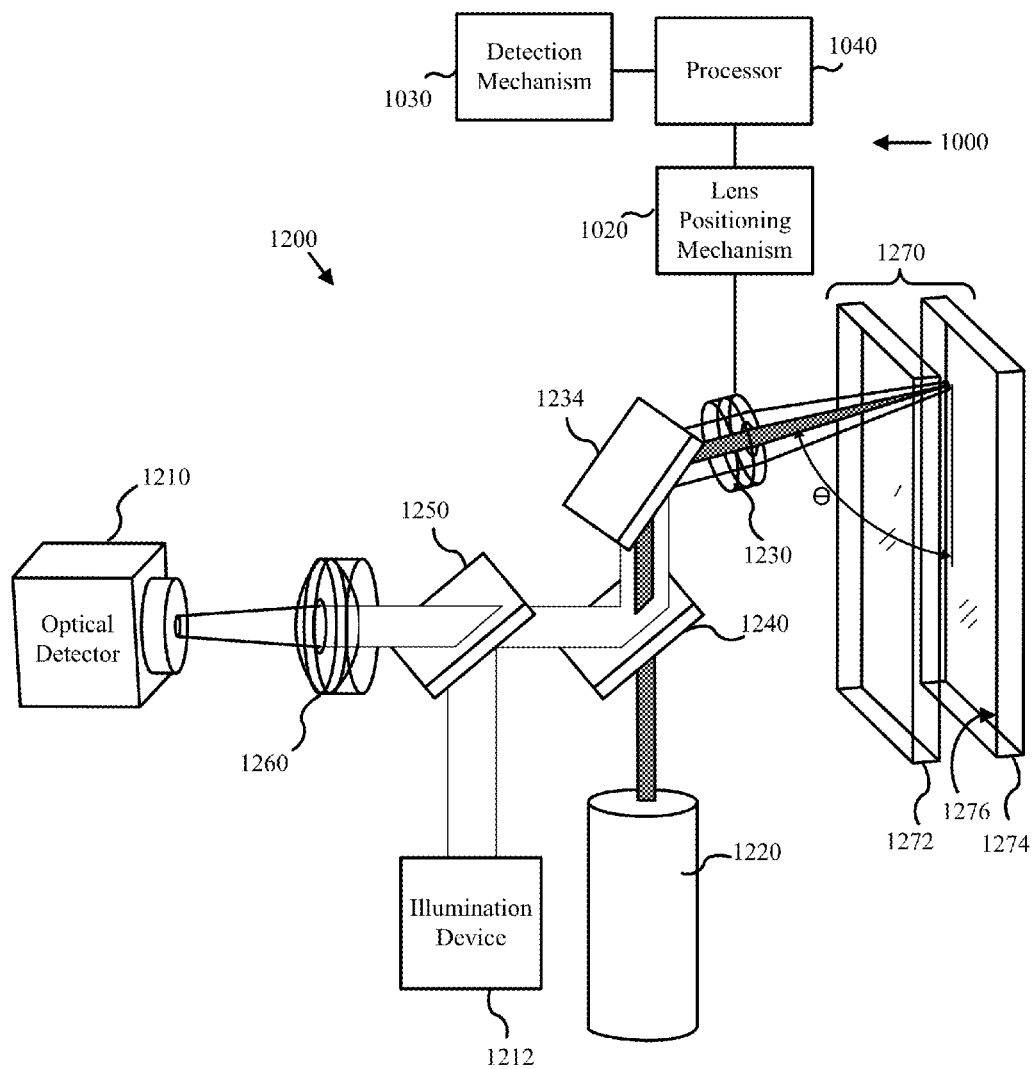
FIG. 11B is a schematic diagram of the optical system of FIG. 11A with the mirror tilted upward.
Figure 12:
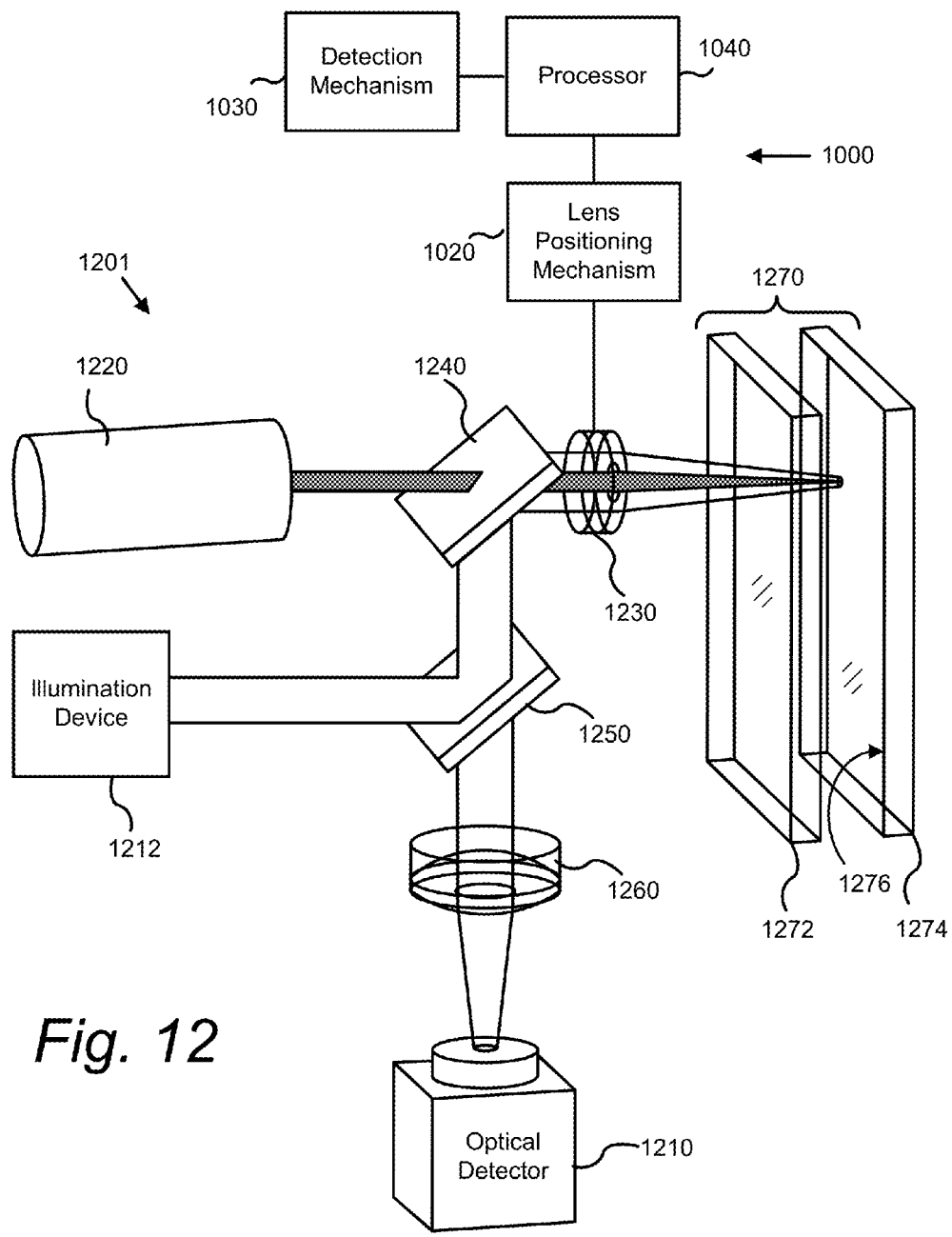
FIG. 12 is a schematic diagram of an optical system in a compact arrangement, according to embodiments.

In FIGS. 11A and 11B, an optical system 1200 includes an optical detector 1210 (e.g., a charge coupled device (CCD), Complementary metal-oxide-semiconductor (CMOS) sensor, etc.), an illumination device 1212, and a laser 1220 serving as a defect mitigator. Both laser 1220 and illumination device 1212 provide collimated light. Optical system 1200 also includes a first lens 1230, a mirror 1234, a first dichroic mirror 1240, a second dichroic mirror 1250, and a second lens 1260. As shown, optical detector 1210, illumination device 1212, and laser 1220 share a coaxial optical path between first dichroic mirror 1240 and mirror 1234 and also between mirror 1234 and first lens 1230. Second lens 1260 may be a condensing lens. First lens 1230 may be an objective lens.

FIGS. 11A and 11B also include an IGU 1270 with a defect (not shown) being imaged and mitigated. The IGU 1270 has a first lite 1272 (first pane) and a second lite 1274 (second pane) with an electrochromic device disposed on a surface 1276 of the second lite 1274. The defect (not shown) being mitigated is located on the surface 1276 of the second lite 1274. In a defect imaging and mitigation operation, the electrochromic device disposed on surface 1276 of IGU 1270 may be transitioned to a colored state.

During the imaging and mitigation operation illustrated in FIGS. 11A and 11B, illumination device 1212 provides collimated illumination light. The illumination light is reflected at about 90 degrees from the second dichroic mirror 1250, and then reflected at about 90 degrees from first dichroic mirror 1240, and then reflected at about 90 degrees from mirror 1234 to first lens 1230 which focuses the illumination light. The focused illumination light passes through the first lite 1272 to the second lite 1274 of the IGU 1270. Illumination light reflected from the second lite 1274 to mirror 1234 will be reflected at about 90 degrees from mirror 1234 and then reflected at about 90 degrees from the first dichroic mirror 1240. This light passes through the second dichroic mirror 1250 to second lens 1260. Second lens 1260 focuses the reflected light to the optical detector 1210. The optical detector 1210 can form an image of the defect based on light reflected from the defect area.

In FIGS. 11A and 11B, the laser 1220 emits light for mitigating the defect. The light from laser 1220 passes through the first dichroic mirror 1240, and is reflected at about 90 degrees from mirror 1234 to the first lens 1230. The first lens 1230 focuses the mitigating light to a focal point. The first dichroic mirror 1240 is specified such that the wavelength or wavelengths of light from laser 1220 passes through the first dichroic mirror 1240. The second dichroic mirror 1250 is specified such that the wavelength or wavelengths of light from illumination device 1212 is reflected by the dichroic mirror 1250. First lens 1230 focuses the collimated light from laser 1220 to a focal point at or near surface 1276 to concentrate the energy of the light to a targeted portion to mitigate the defect. First lens 1230 also focuses the collimated light from illumination device 1212 to a focal point on or near to surface 1276. In this optical system 1200, there is a common axis (coaxial path) of the laser and illumination light from the first dichroic mirror 1240 to the mirror 1234 and from the mirror 1234 through the first (focal) lens 1230, and then to the focal point.

In FIGS. 11A and 11B, mirror 1234 and first lens 1230 can be rotated together about a pivot point (or alternatively about one or more rotating axes) to direct the light from first lens 1230 at different angles. This rotation allows the light to be directed at angles to be able to locate the focal point, for example, under a spacer at the edge of an IGU or to the corner of the IGU. In FIG. 11A, mirror 1234 and first lens 1230 are located at a nominal position to direct the optical path at about a 90 degree angle to a plane substantially parallel to the surface 1276. In FIG. 11B, mirror 1234 and first lens 1230 are tilted upward to direct the optical path at an angle θ with respect to the plane substantially parallel to the surface 1276.

As shown, light from laser 1220 and illumination device 1212 is collimated and along a coaxial path to the first lens 1230. Since the light received at the first lens 1230 is collimated and coaxial, the first lens 1230 can focus both the mitigating and imaging light to an aligned focal point. Also, moving the first lens 1230 along the optical path axis can control the location of the focal point of both the laser light and imaging light. That is, the position of the first lens 1230 along the coaxial optical path can be adjusted to finely focus laser 1220, optical detector 1210, and illumination device 1212. The optical system 1200 and other similar optical systems having a coaxial optical path of collimated light allow the laser to be aimed at the defect and provide accurate alignment of the detection and mitigation processes. In these optical systems, laser 1220, optical detector 1210, and illumination device 1212 can be automatically focused with a dynamic autofocus system disclosed herein. To illustrate this aspect, FIGS. 11A and 11B also include a dynamic autofocus system 1000 having a lens positioning mechanism 1020, a detection mechanism 1030, and a processor 1040 in communication with lens positioning mechanism 1020 and detection mechanism 1030. Lens positioning mechanism 1020 is in communication with the first lens 1230 to move the first lens 1230 to maintain the focal points at the same distance from the first lens 1230 as the IGU 1270 may flex or otherwise move during the process.

In FIG. 12, an optical system 1201 includes an optical detector 1210 (e.g., a charge coupled device (CCD), complementary metal-oxide-semiconductor (CMOS) sensor, etc.), an illumination device 1212, and a laser 1220 serving as a defect mitigator. Both laser 1220 and illumination device 1212 provide collimated light. Optical system 1200 also includes a first lens 1230 (e.g., objective lens), a first dichroic mirror 1240, a second dichroic mirror 1250, and a second lens 1260 (e.g., condensing lens). As shown, optical detector 1210, illumination device 1212, and laser 1220 share a coaxial optical path between first dichroic mirror 1240 and first lens 1230. FIG. 12 also includes an IGU 1270 with a defect (not shown) being imaged and mitigated. The IGU 1270 has a first lite 1272 (first pane) and a second lite 1274 (second pane) with an electrochromic device disposed on a surface 1276 of the second lite 1274. The defect being mitigated is located on the surface 1276 of the second lite 1274.

During the imaging and mitigation operation illustrated in FIG. 12, illumination device 1212 provides collimated illumination light. The illumination light is reflected at about 90 degrees from the second dichroic mirror 1250, and then reflected at about 90 degrees from first dichroic mirror 1240 to first lens 1230 which focuses the illumination light. The focused illumination light passes through the first lite 1272 to the second lite 1274 of the IGU 1270. Illumination light reflected from the second lite 1274 to the first dichroic mirror 1240, which is reflected at about 90 degrees to second dichroic mirror 1250. The light passes through the second dichroic mirror 1250 to second lens 1260. Second lens 1260 focuses the reflected light to the optical detector 1210. The optical detector 1210 can form an image of the defect based on light reflected from the defect area.

In FIG. 12, the laser 1220 emits light for mitigating the defect. The light from laser 1220 passes through the first dichroic mirror 1240, and is reflected at about 90 degrees from mirror 1234 to the first lens 1230. The first lens 1230 focuses the mitigating light to a focal point. The first dichroic mirror 1240 is specified such that the wavelength or wavelengths of light from laser 1220 passes through the first dichroic mirror 1240. The second dichroic mirror 1250 is specified such that the wavelength or wavelengths of light from illumination device 1212 is reflected by the dichroic mirror 1250. First lens 1230 focuses the collimated light from laser 1220 to a focal point at or near surface 1276 to concentrate the energy of the light to a targeted portion to mitigate the defect. First lens 1230 also focuses the collimated light from illumination device 1212 to a focal point on or near to surface 1276. In this optical system 1200, there is a common axis (coaxial path) of the laser and illumination light from the first dichroic mirror 1240 to the mirror 1234 and from the mirror 1234 through the first (focal) lens 1230, and then to the focal point.

As shown, light from laser 1220 and illumination device 1212 is collimated and along a coaxial path to the first lens 1230. Since the light received at the first lens 1230 is collimated and coaxial, the first lens 1230 can focus both the mitigating and imaging light to an aligned focal point. Also, moving the first lens 1230 along the optical path axis can control the location of the focal point of both the laser light and imaging light. That is, the position of the first lens 1230 along the coaxial optical path can be adjusted to finely focus laser 1220, optical detector 1210, and illumination device 1212. The optical system 1201 and other similar optical systems having a coaxial optical path of collimated light allow the laser to be aimed at the defect and provide accurate alignment of the detection and mitigation processes. In these optical systems, laser 1220, optical detector 1210, and illumination device 1212 can be automatically focused with a dynamic autofocus system disclosed herein. To illustrate this aspect, FIG. 12 also includes a dynamic autofocus system 1000 having a lens positioning mechanism 1020, a detection mechanism 1030, and a processor 1040 in communication with lens positioning mechanism 1020 and detection mechanism 1030. Lens positioning mechanism 1020 is in communication with the first lens 1230 to move the first lens 1230 to maintain the focal point at the same distance from the first lens 1230 as the IGU 1270 may flex or otherwise move during the process.

In the optical systems shown in FIGS. 11A and 11B, FIG. 12, in FIGS. 13A-I, and other disclosed embodiments, the propagated light from the laser and optical detector are provided along a common axis from one side of the IGU. This arrangement allows the option of including a pivot system for swiveling one or more components of the optical system around to image and mitigate defects to reach corners or underneath spacers (not shown) at the edges of the IGU. For example, such as pivot system can be used to swivel or otherwise rotate the mirror 1234 described with reference to FIGS. 11A and 11B.

Portable Defect Mitigator Subsystems

Certain embodiments of portable defect mitigators disclosed herein may include one or more of the following subsystems: 1) X-Y stage for moving the optical system with respect to the window surface to increase the field of view; 2) one or more Z-stages for moving the focal point; 3) tether system; 4) a vacuum engagement system for affixing the portable defect mitigator to the surface of the window; 5) a dynamic autofocus system; 6) imaging and mitigation subsystems which share a common axis from a dichroic mirror through the focal lens and onto the window surface, 7) a pivot system for pivoting the optics in a portable defect mitigator mounted to the window in order to image and mitigate defects at the corners or underneath a spacer of an IGU; 8) a chassis; 9) case-like structure with a separate chassis; 10) a tracking stylus; and 11) a beam blocker.

An example of a portable defect mitigator 1400 with many of the above-listed subsystems can be found described below with reference to FIGS. 13A-I. Other examples of the above-listed subsystems can be found throughout the disclosure. For example, a dynamic autofocus system is described in a section above. As another example, imaging and mitigation subsystems which share a common axis from a dichroic mirror through the focal lens and to surface of a window are described above with reference to FIG. 11A, FIG. 11B, FIG. 12, and FIG. 5C. As another example, a pivot system is described below with reference to FIG. 11A and FIG. 11B. In certain embodiments, the portable defect mitigators described with reference to FIGS. 13A-I and FIG. 14 may include the optical system described with reference to FIGS. 11A, 11B, and 12.

—Chassis

The chassis is of a compact and low weight design for handheld operation by the user. In one example, the chassis structure and its contents weigh about 10 pounds. Although the chassis structure may be of any shape, the chassis of certain implementations is in the general shape of a rectangular box. In some cases, the chassis structure may be made of a low weight material such as, for example, carbon-fiber based composite materials. In most cases, the chassis is designed as a light-tight enclosure to ensure that laser light does not leave the chassis during mitigation for safety concerns. The chassis may include one or more handles to facilitate portability. The handles are designed to allow the operator to affix the chassis to the window surface. The chassis has components designed to mate and engage the portable defect mitigator to the surface of the window during operation.

Figure 13A:
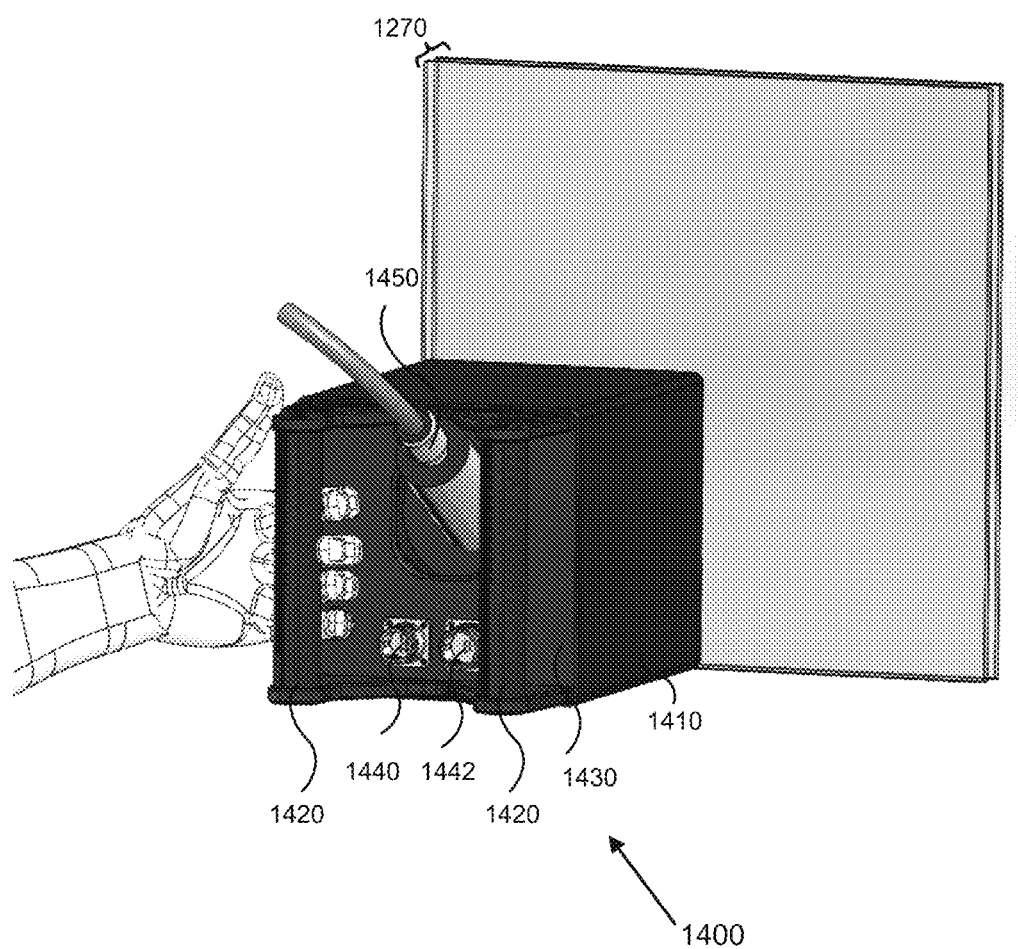
FIGS. 13A-H are isometric line drawings of a portable defect mitigator, according to embodiments.

FIG. 13A is an isometric drawing a portable defect mitigator 1400 including a box-shaped chassis 1410, according to an embodiment. In the illustrated embodiment, the chassis 1410 is a light tight enclosure. The chassis 1410 is in a general form of a box having approximate dimensions of 7.5 inches×7.5 inches on the face for engaging the window and 8 inches in width. In other embodiments, the chassis may be of a smaller size. In the illustrated example, the chassis 1410 in the process of being affixed to an IGU 1270 having two electrochromic lites. The chassis 1410 in the illustration is a carbon-fiber based design and the chassis and its contents weigh about 10 lbs.

The chassis 1410 includes two handles 1420. Each handle 1420 is attached at two ends to two flanges connected along opposing edges of a surface 1430 of the chassis 1410. The chassis 1410 also includes two ports 1440, 1442 extending from the back surface 1430. The first port 1440 may be a vacuum port for attaching a vacuum line. The other end of the vacuum line may be connected to a vacuum device. The second port 1442 may be a power port for connecting a power line. The power line may be connected to a power source. The chassis 1410 also includes a protruding portion having an input port 1450.

—Separate Case

In certain embodiments, a portable defect mitigator will include two main portions: 1) a first portion with a case-like (e.g., briefcase-like, suitcase-like, etc.) structure that holds the electronics, software, and optionally a user interface, and 2) a separate second portion with a chassis containing components of the optics system, the dynamic autofocus system, stages for the optical components, and devices for affixing the chassis to the surface of the window. In some implementations, the laser is in the case-like structure. In other implementations, the laser is in the separate chassis. The chassis portion is separate from the case-like structure and is typically in a compact and light-weight design that can be handheld during operation. The chassis portion is designed to mate and engage to the surface of the window to be remedied. While the case-like portion may also be handheld, it is designed to contain the heavier and bulkier components of the portable defect mitigator. This allows the chassis portion to be lighter, easily maneuverable by the operator, and capable of being affixed to the surface of the window during operation.

Components within the chassis may be in communication with components within the case-like structure through one or more connectors. For example, there may be a fiber-optic cable between the laser in the case-like structure and the optics in the separate chassis to propagate light from the laser through the optics to mitigate the defect at the window. As another example, there may be a vacuum line between a vacuum device in the case-like structure and the vacuum system in the chassis to apply a vacuum to the vacuum system holding the chassis to the window during defect imaging and mitigation. In yet another example, there may be a power line between a power source in the case-like structure and the chassis.

—Tether

In certain embodiments, the portable defect mitigator may include a tether system for added safety. The tether subsystem may include a vacuum device (e.g., suction cup) that is connected to a tether line. The tether line is attached to the portable defect mitigator, for example, at the portion of the chassis facing upward. Some examples of devices that can be used as tether lines include a cable, a spring-loaded reel, or a reel counterbalance. The vacuum device may be attached to a structure located above the defect area such as, for example, a wall above the electrochromic window or a portion of the electrochromic window itself. The vacuum device can provide an anchor and provides an upward force to the tether line that can take some moment off the laser head and/or the engagement system (e.g., the vacuum engagement system discussed below) used to affix the portable defect mitigator to the window. In addition, the tether system can provide a safety line that can hold the portable defect mitigator if the engagement system fails or if the mitigator is dropped when moving it from one defect area to another defect area on the window.

—Vacuum Engagement System

In certain embodiments, the portable defect mitigator includes a vacuum engagement system for affixing the chassis to the surface of the window during the defect imaging and mitigation procedure. The vacuum engagement system is designed to make a substantially rigid engagement between the window and the portable defect mitigator.

Figure 13B:
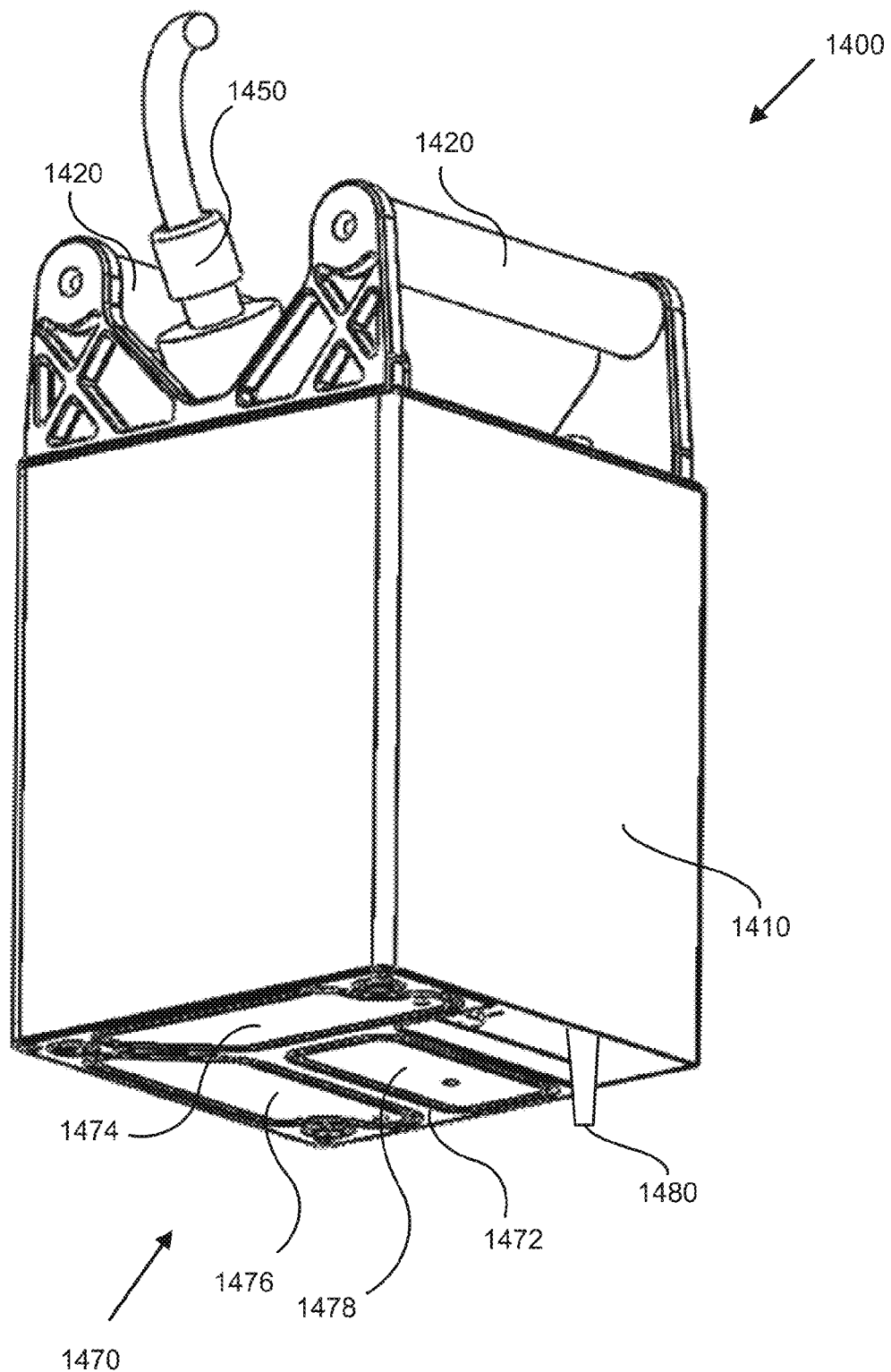

FIG. 13B is an isometric drawing of the portable defect mitigator 1400 depicted in FIG. 13A. In this illustration, the portion of the portable defect mitigator 1410 that engages the window in shown. This portion includes a vacuum engagement system 1470 with O-rings for affixing the portable defect mitigator 1400 to a surface of a window. The vacuum engagement system 1470 includes a mating base plate 1472 having a plurality of three shallow low-profile recessed regions 1474, 1476, 1478 (e.g., recesses) and a circumferential groove around each region. In other embodiments, the plurality of recesses may have other numbers of recesses (e.g., two or more). Each of the low-profile regions 1474, 1476, 1478 can from a vacuum seal with the window using O-rings or other sealing member that fit into the circumferential grooves. When mating to the window surface, each of the low-profile regions 1474, 1476, 1478 forms a separate shallow vacuum chamber with the window. Each one of the low-profile regions 1474, 1476, 1478 is designed (e.g., with a large enough area and depth) to create a vacuum chamber sufficient (i.e. with enough suction force) to hold the chassis portion onto the surface of the window during mitigation. Based on this triple safety design, if any two of the vacuum chambers loses vacuum, the remaining vacuum chamber can hold the chassis 1410 engaged with the window. For additional safety, each of the vacuum chambers is separately controllable (e.g., by a set of valves) and isolated, so that if any one of the vacuum chambers loses vacuum, the other two chambers do not similarly lose vacuum and can keep the chassis 1410 engaged with the window. For example, the system may have a set of valves. Each valve controls vacuum in a single chamber associated with that valve. In some cases, the valves may be independently controlled.

In this illustration, a laser beam 1480 is shown extending from the surface of the chassis 1410 through an area separate from the low-profile regions 1474, 1476, 1478. In some cases, the vacuum engagement system 1470 may also include a feedback control system that determines if one or more of the chambers loses vacuum. If one or more vacuum chambers loses vacuum, the feedback control system can send a shutoff signal to the laser, which may provide additional safety.

In certain implementations, the portable defect mitigator may employ a Class 4 laser for defect mitigation. In these cases, there may be a potential risk if the mitigator disengages from the window during mitigation that the laser beam directed outside the light tight enclosure can potentially cause injury. The triple safety vacuum engagement system 1470 of FIG. 13B and engagement systems of other disclosed embodiments can help ensure that the portable defect mitigator does not disengage from the window during defect mitigation.

In some cases, a tether system describe herein may also be included to provide additional safety if the engagement system disengages. In other cases, a low power consumption laser may be used, which allows for a non-tethered defect mitigator. In one of these cases, the low-profile regions 1474, 1476, 1478 cavities may be welded to form a plenum that could store vacuum, enabling the use of a very small pump to pump out the plenum and be valved to and then stuck to the window. Although a high velocity vacuum may be need to provide the initial suction to the window in a short amount of time, very little vacuum is required to maintain the vacuum once affixed to the window. Having a storage volume can enable using a vacuum pump on board and could go along with enabling the use of a diode or low power consumption laser thus having a non-tethered defect mitigator.

—X-Y Stage and Z Stages Position Adjustments

In certain embodiments, the field of view of the optical detector (e.g., camera) in a portable defect mitigator may be a relatively small area (e.g., an area of about 7 mm×7 mm). To widen the field of view of the optical detector and also to be able to move the laser over a larger area, the portable defect mitigator may include an X-Y stage and/or or Z-stage that can move relative to the window onto which the portable defect mitigator is mounted. The X-Y stage is associated with movement in a plane that is parallel to the surface of the window. The Z-stage is associated with movement normal to the plane parallel to the surface of the window.

The optical system or components (e.g., laser and/or optical detector) of the optical system can be mounted to an X-Y stage to widen the field of view of both the optical detector and the laser. By using such X-Y stage, a portable defect mitigator affixed to the window can have a wide imaging and mitigating area. In some embodiments, an X-Y stage may be able to move the optical system over an area of the window surface in the range of between 7 inches×7 inches. The X-Y stage can be mounted to a Z-stage. The Z-stage can provide movement toward and away from the window surface. In some embodiments, a portable defect mitigator includes two Z-stages: 1) a first stage for adjusting the optics to roughly locate the focal point at a surface of IGU; and 2) a second Z-stage for focusing the optics. The first stage may have a wider range of movement (e.g., 1 inch, 1.5 inches, 2 inches, etc.) than the second stage.

Figure 13C:
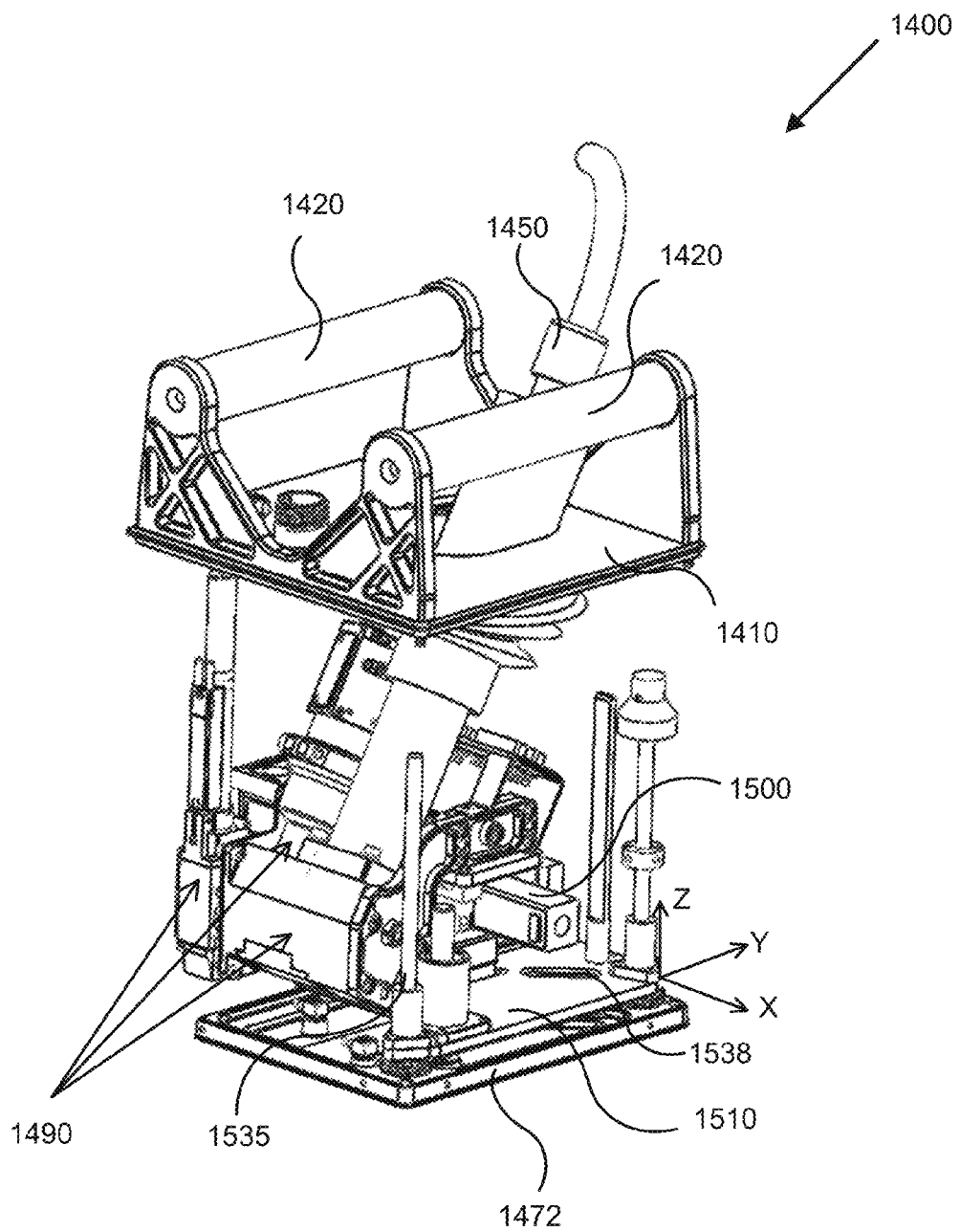

FIG. 13C is an isometric drawing of components of the portable defect mitigator 1400 depicted in FIGS. 13A and 13B. In this illustrated example, the side and back panels of the chassis 1410 have been removed to view the components within. These components include an optical system 1490 mounted to an X-Y stage 1500. The X-Y stage is connected to a first Z-stage 1510. The Z-stage includes X-axis, Y-axis, and Z-axis at the corner. The Z-stage 1510 has cutouts that slidably connect to three linear screws 1535 affixed at one end to the base plate 1472 of the chassis 1410. This connection allows the stage mounting plate 1510 to move in the Z direction with respect to the base plate 1472 and the window, which will be described in more detail below in reference to FIGS. 13D and 13E. The X-Y stage 1500 can move in the X-direction and Y-direction relative to the first Z-stage 1510 and the first Z-stage 1510 can move in the Z-direction relative to the base plate 1472. The potable defect mitigator 1400 also includes a second Z-stage that is a component of a dynamic autofocus system. In the illustrated example, the X-direction refers to both the positive and negative direction in an axis parallel to the X-axis, the Y-direction refers to both the positive and negative direction in an axis parallel to the Y-axis, and the Z-direction refers to both the positive and negative direction in an axis parallel to the Z-axis.

Figure 13D:
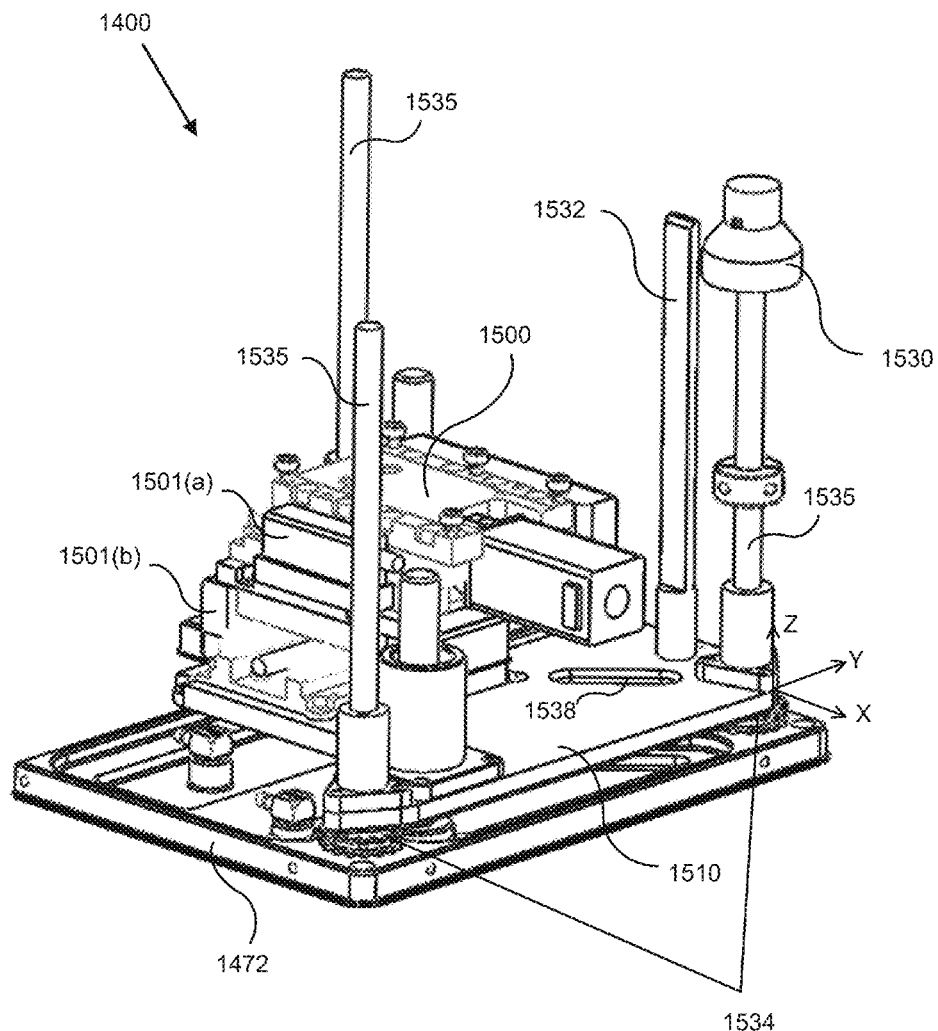
Figure 13E:
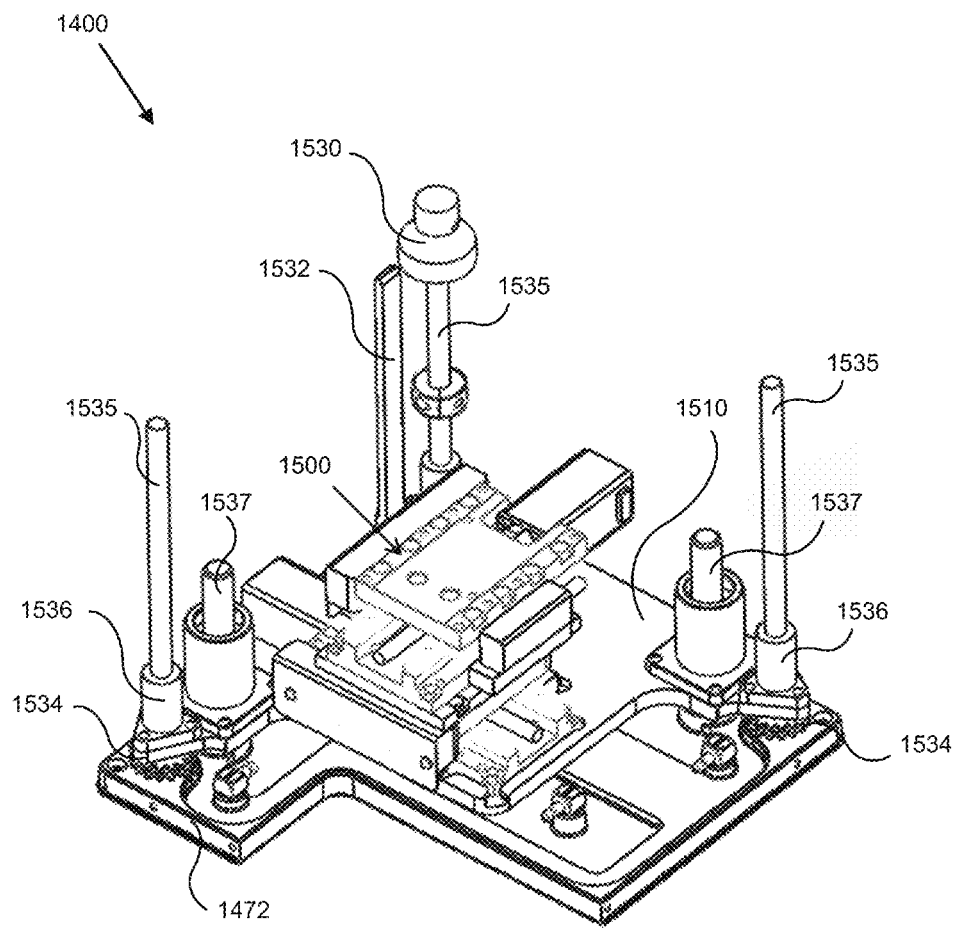

FIGS. 13D and 13E are isometric drawings of components of the portable defect mitigator 1400 depicted in FIGS. 13A-C. In FIGS. 13D and 13E, the chassis 1410 and the optical system 1490 have been removed to view the X-Y stage 1500 and other components of the portable defect mitigator 1400. The portable defect mitigator includes a mechanism (e.g., a high speed motor) that controls the movement of the X-Y stage 1500 and the mounted optical system 1490 in the X-direction and in the Y-direction relative to the surface of the window.

The X-Y stage 1500 includes two sliding platforms 1501(*a*) and 1501(*b*). Sliding platform 1501(*a*) can slide in the X-direction within a set of rails. Sliding platform 1501(*b*) slides in the Y-direction within a set of rails. The X-Y stage 1500 includes two mechanisms for rotating threaded rods. The first mechanism rotates a first threaded rod to engage and translate sliding platform 1501(*a*) in the X-direction. The second mechanism rotates a second threaded rod to engage and translate sliding platform 1501(*b*) in the Y-direction. The first and second mechanisms controlling the threaded rods can be manually controlled by the operator or automatically controlled by an actuator that receives control signals from a processor of the portable defect mitigator 1400. For example, these mechanisms can be a linear motor, manual linear actuator, etc. In the illustrated embodiment, the field of vision of the optical detector in the optical system 1490 is about 7 mm×7 mm at the surface of the electrochromic device. By employing the X-Y stage 1500, the field of vision of the optical detector and laser is increased to 22 mm×22 mm.

The portable defect mitigator 1400 also includes a thickness adjustment knob 1530, a glass thickness indicator 1532, a belt and gear assembly 1534, and three linear screws 1535, and two posts 1537 (shown in FIG. 13E). These components are used to adjust the Z-direction coordinate of the optical system 1490 to calibrate the optical system 1490 according to the thickness of the window being mitigated. In one case, the Z-direction coordinate can be adjusted to locate the focal point of the laser at a surface of the electrochromic device of an electrochromic window in an IGU before the window flexes. The Z-direction coordinate is adjusted by rotating the thickness adjustment knob 1530. In one case, the thickness adjustment knob 1530 may be rotated to align a marker on the thickness adjustment knob 1530 to an appropriate indicator on the glass thickness indicator 1532. The glass thickness indicator 1532 may have a series of indicators that designate different thicknesses.

This adjustment may be based on one or more window parameters such as, for example, the thickness of the insulated glass unit, the thickness of the window unit, the thickness of the spacer, the thickness of each pane or lite, etc. In one embodiment, the adjustment may be based on the standard thickness of the window (or IGU) and/or the thickness between the surface of the engaged lite to the surface of the electrochromic device having the defect. The adjustment can be used to calibrate the starting position of the focal point of the laser. For example, if the defect is located on an electrochromic device of an outer lite (non-engaged lite) of an IGU having multiple lites, the thickness adjustment knob 1530 can be used to calibrate the starting position of the focal point of the laser at a surface of the electrochromic device of the outer lite. If the defect is located on an electrochromic device of the engaged lite, the thickness adjustment knob 1530 can be used to calibrate the starting position of the focal point at the electrochromic device of the outer lite. This adjustment is generally made before initiating the defect imaging and mitigation process. Once this process starts, a dynamic autofocus system 1000 shown with respect to FIG. 9 can be used to make fine adjustments to the Z-position of the focal point to accommodate for flexing or other movement of the window. In some cases, an LED or other type of indicator can be used in concert with the dynamic autofocus system or other means of measuring glass thickness described herein to precisely adjust the Z-position either manually or automatically where the linear screws 1535 can be turned by electric motors.

The belt and gear assembly 1534 includes a series of gears engaged to move by at least one belt. One of the gears is a master gear affixed to an end of a linear screw 1535 having the glass thickness adjustment knob 1530 at the opposing end. Rotating the glass thickness adjustment knob 1530 rotates the master gear at the end of the linear screw 1535, which moves the belt, which rotates the other gears including slave gears attached to the other linear screws 1535. Thus, rotating the glass thickness adjustment knob 1530 effects equivalent and simultaneous rotation of all three linear screws 1535. The linear screws 1535 include a threaded portion at the end proximal the mounting plate 1510. The threaded portion of the linear screws 1535 movably engages a linear screw nut 1536 affixed to the mounting plate 1510. As the linear screws 1535 are rotated using the glass thickness adjustment knob 1530, the mounting plate 1510 translates in the Z-direction guided by the two posts 1537 with linear bearings to adjust the Z-position of the mounting plate 1510. The portable defect mitigator 1400 also includes a guide shaft 1537 between the base plate 1472 and the stage mounting plate 1510. The portable defect mitigator 1400 also includes an optional belt tensioner 1538. The belt tensioner 1538 allows an idle gear to be moved on a slide to tighten the belt.

In one embodiment, the portable defect mitigator 1400 may include a system where the linear screws 1535 can be turned by electric motors. For example, a triangulation sensor may provide feedback to indicate when to stop moving the linear screws 1535.

Figure 13F:
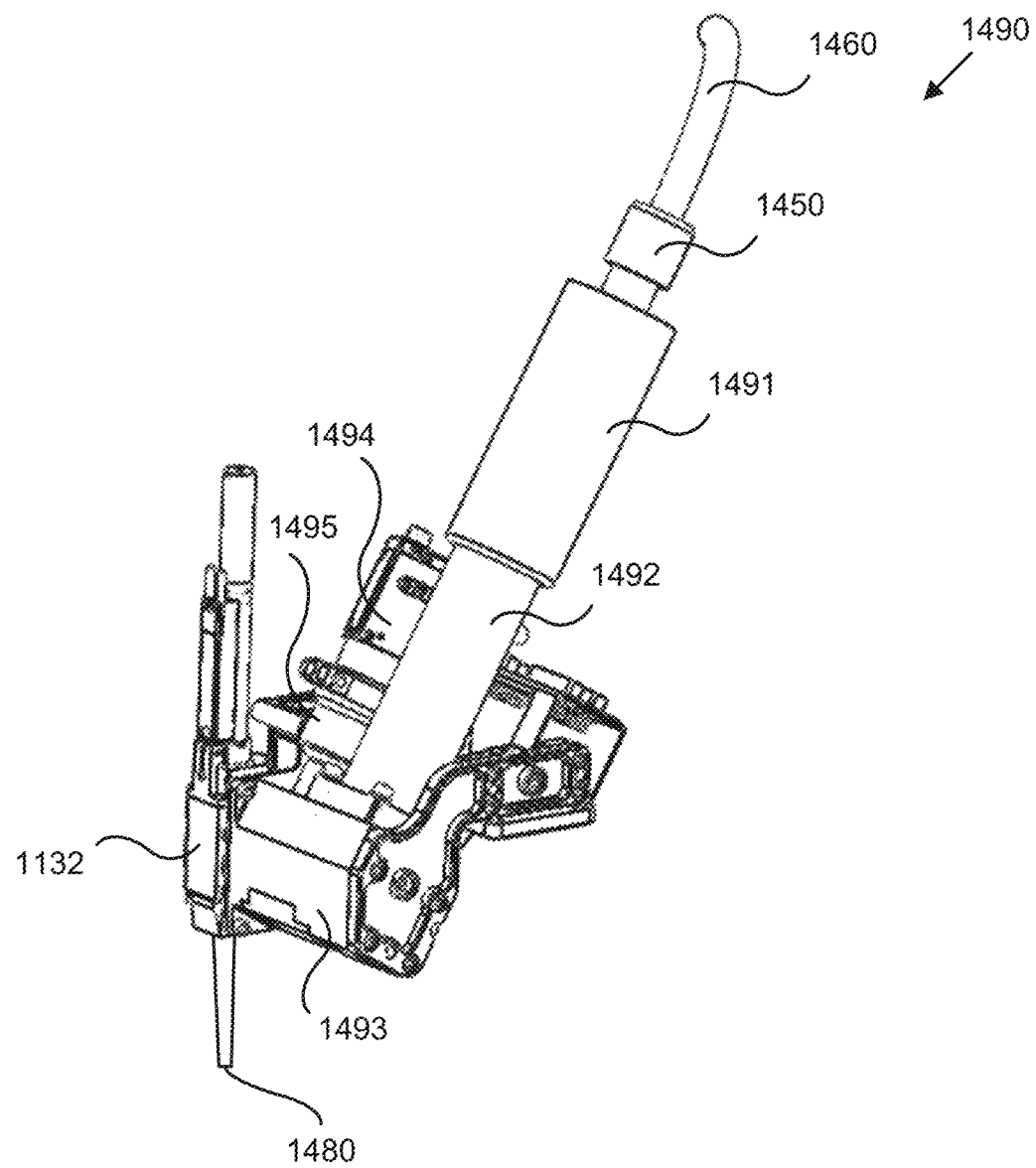
Figure 13G:
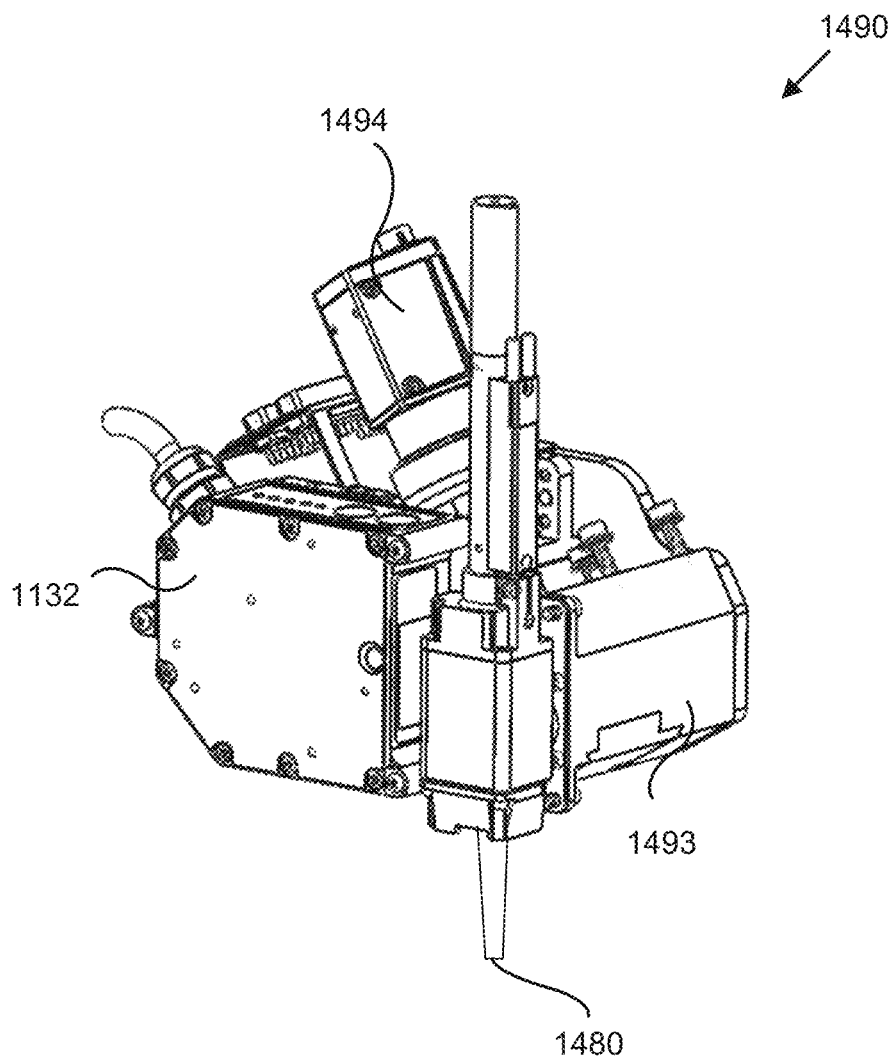
Figure 13H:
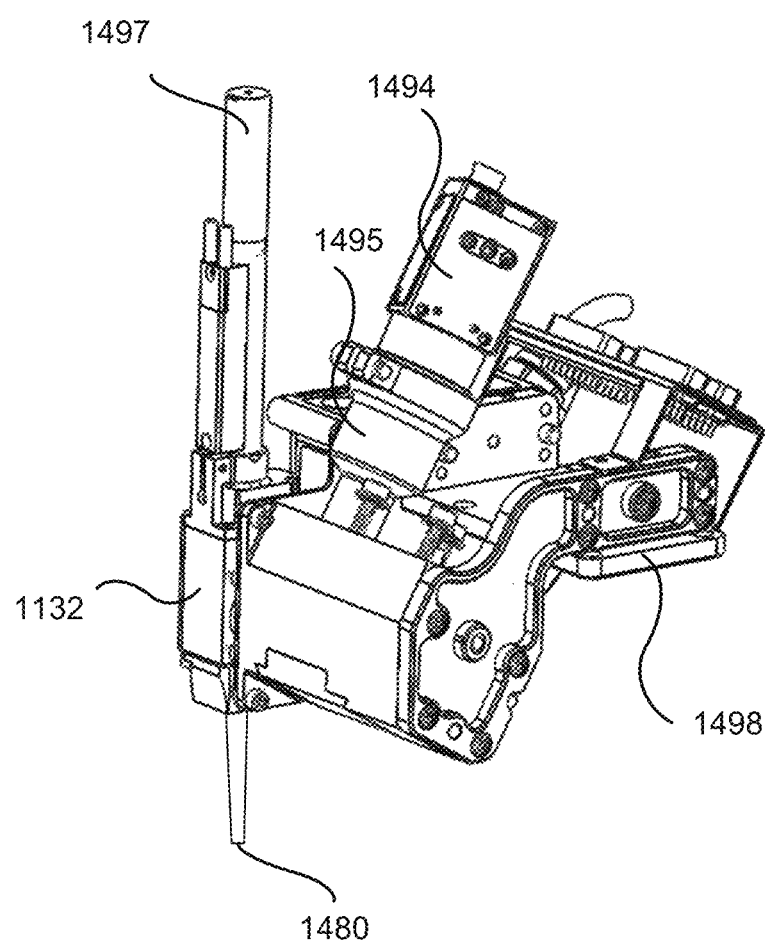

The portable defect mitigator 1400 depicted in FIGS. 13A-E also includes an optical system 1490 with a similar arrangement to that of the optical system 1200 depicted in FIG. 11. FIGS. 13F, 13G, 13H are isometric drawings of components of optical system 1490. Optical system 1490 includes a laser input 1491 and a laser optics block 1492 in communication with laser input 1491. Laser input 1491 includes port 1450 connected to optical fiber 1460. Laser optics block 1492 is in communication with a main optics block 1493. The optical system 1490 also includes an optical detector 1494 (e.g., camera), a vision optics block 1495, and a dynamic autofocus system having a triangulation sensor 1132. The autofocus system is similar to the dynamic autofocus system 1000 describe with reference to FIG. 9 and includes triangulation sensor 1132.

In the optical system 1490, there is a coaxial optical path between the laser input 1491 and the detection optics 1494 to align the detection and mitigation processes. In addition, collimated light is provided from the laser and optical detector along the coaxial path to the focusing lens. This arrangement allows the dynamic autofocus system to adjust the focusing lens to dynamically focus both the laser and optical detector to the same focal point 1480 as the window may flex during the imaging and mitigation process.

—Pivot System

In some cases, defects can be concentrated near the edges of an electrochromic window in an IGU. This can sometimes be the result of scribing processes performed on a fabricated window. While the spacer at the edges of the IGU may partially obscure these edge defects, the penumbra or halo around the defects may well extend into the viewable area inside the footprint between the spacers.

Embodiments disclosed herein include a portable defect mitigator that can mitigate defects underneath the spacer and at the corners. These portable defect mitigators may be particularly effective in mitigating defects in a cantilevered spacer design, which allows greater access by defect mitigation optics to reach underneath the spacer. An example of a cantilevered spacer design and other spacer designs can be found in patent application Ser. No. 61/421,154, filed on Dec. 28, 2010, entitled "Improved Separators for Insulated Glass Units," which is hereby incorporated by reference in its entirety.

The optical systems shown in FIGS. 11A-11B, in FIG. 12, and in FIGS. 13A-H, and in other disclosed embodiments are particularly adaptable to pivot the focal point of the laser to mitigate under the spacer and at the corner. In these systems, the propagated light from the laser 1220 and optical detector 1210 are provided along a common axis path from one side of the IGU. This arrangement allows the option of including a pivot system for pivoting the final optics path of the laser and vision together to image and mitigate defects to reach corners or underneath spacers at the edges of an IGU. Basically, the pivot system allows for pivoting around the laser dot on the dichroic mirror surface in any direction. In one embodiment, a pivot system includes a pivot mechanism (e.g., motor) that can control the rotation of the mirror 1234 and the first lens 1230 described with respect to FIGS. 11A and 11B. Another example of a pivot system includes a mechanism for pivoting the dichroic mirror (e.g., dichroic mirror 1240) and the focal lens (e.g., lens 1230) as a unit along an axis in a plane parallel to a plane approximating the surface of the electrochromic device. For example, the pivot system could pivot the X-Y stage 1500 about one or more axes lying in the X-Y plane, which is parallel to the plane approximating the surface of the window.

In embodiments having a pivot system, the laser beam is pivoted at an angle, which could reflect off a back plate and out of the light tight enclosure of the chassis. In these embodiments, the portable mitigator may include a light blocking material (e.g., hat, sleeve, etc.) placed skirting out from the side of the chassis to extend the light tight area and provide side protection from the laser beam.

—Tracking Stylus

In certain embodiments, a portable defect mitigator will include a tracking stylus to set the coordinates of the focal point for mitigating the defect. For example, a user can place the tracking stylus at or near one or more defects of an electrochromic window in a tinted state to define the coordinates of the one or more defects. The defect(s) coordinates can be communicated to a processor which determines a set of instructions for automatically mitigating the one or more defects. These instructions may include information for operating the laser and for moving the laser to the coordinates. These instructions may be communicated to the motor controlling the X-Y stage, the pivot system, and/or other system for locating the focal point of the laser at the coordinates of the defects. The set of instructions is also communicated to the laser to control the timing and energy of the emissions from the laser.

—Beam Blocker

In certain embodiments, a portable defect mitigator may include a beam blocker. The beam blocker is affixed to an outer surface of the IGU adjacent the defect being mitigated. The outer surface is opposite the surface of the IGU to which the portable defect mitigator is attached. The beam blocker reflects or blocks the laser light from exiting through the outer surface to address safety concerns. The beam blocker may also be used as a detection mechanism 1030 to measure the distance to the surfaces within the IGU. In this case, other detection methods may be employed such as ultrasonic, capacitive, or other laser measurement techniques. Using a beam blocker may be a less expensive alternative to using an internal triangulation sensor.

Exemplary Method of Defect Imaging and Mitigation

Figure 14:
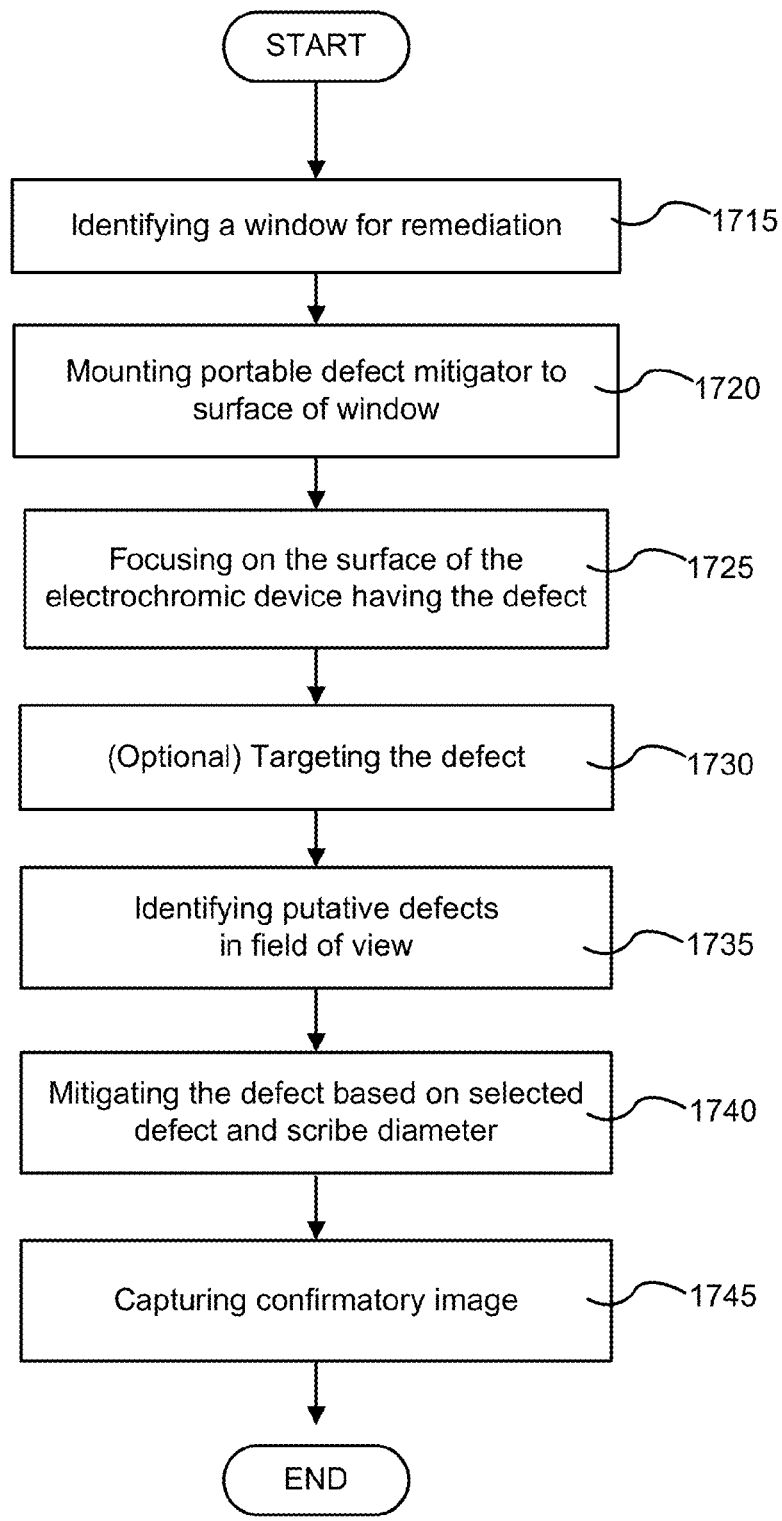
FIG. 14 is a flowchart of a method of using a portable defect mitigator, according to embodiments.

FIG. 14 is a flowchart of a method of defect imaging and mitigation, according to embodiments. At step 1715, a window is identified for defect remediation. In some cases, this may involve a human detecting a halo or other perceptible defect in a window in the tinted state. The human may visually inspect or use a magnification device (e.g., microscope) to determine whether there is a defect. In other cases, the defect may be determined by an automated detection system that uses a light detector to measure light transmitted through the window in the tinted state to identify the window for remediation. In yet other cases, the defect may be determined using thermal imaging such as, for example, lock-in thermography.

At step 1720, a portable defect mitigator is mounted to the surface of the window near the region where the defect was observed. For example, the chassis portion 1410 of the portable defect mitigator 1440 can be affixed as shown in FIG. 13A to a surface of an electrochromic window. The portable defect mitigator can be mounted to the surface using various attachment methods. For example, the portable defect mitigator may be mounted to the surface using a vacuum engagement system such as, for example, triple safety vacuum engagement system 1470 described in reference to FIG. 13B that forms three isolated vacuum chambers with the surface, each capable of holding the chassis 1410 to the window. As another example, the portable defect mitigator may be mounted to the surface using a mechanical clamp.

At step 1725, the imaging system of the portable defect mitigator is brought into focus with the surface of the electrochromic device. A sharp image of the surface is generated at the optical detector (e.g., camera) when the focal lens and the surface of the electrochromic device are separated by the focal length of the lens. Moving the lens to the proper separation can be accomplished either manually or automatically. In one example, the portable defect mitigator may have an autofocus device that can move the lens to the proper focal length. In another example, the operator may move the lens manually to focus on the surface. In yet another example, an operator using a portable defect mitigator 1400 depicted in FIGS. 13A-H may rotate a thickness adjustment knob 1530 to move the focal point of the laser near or at the surface of the electrochromic device based on a standard thickness of the electrochromic window or IGU. In some cases, this is an approximation and only roughly places the focal point at the surface. This is used when remedying defects in an IGU. The rough approximation is a starting point to ensure that the focal point is at the correct surface of an IGU. The operator or automated system can finely tune the focus to the plane at the surface once the focal point is close to the surface. This helps to ensure that the defect mitigator is focused on the correct electrochromic device where there may be more than a single electrochromic device, for example, in an IGU.

At step 1730, the optical system of the portable defect mitigator optionally targets the defect area within the field of view of the image and mitigation system. In some cases, the optical system may be moved in the x-direction and the y-direction to center or otherwise locate field of view of the optical detector and laser proximal the defect. For example, the portable defect mitigator 1400 depicted in FIGS. 13A-H includes an X-Y stage for moving the optical system in the X-direction and the Y-direction. The X-Y stage can be moved so that the defect is at or near the center of the field of view. In some embodiments, step 1730 is performed prior to step 1725.

Once the image system is properly focused on a field of view of the electrochromic device surface, the putative defects within the field of view are identified (step 1735). A processor (e.g., microprocessor) in the portable defect mitigator may process code or other logic having instructions to identify the putative defects within the field of view based on the intensity of light detected as passing through particular regions in the field of view. The logic may also include instructions to identify the putative defects by location and intensity or other characterizing parameters (e.g., wavelength, etc.) of the light. The processor may also process code having instructions that define a scribe circle or other scribe pattern around the putative defect. Alternatively, the user can specify a scribe circle or other scribe pattern using a user interface. Some examples of variations on a simple circular scribe pattern can be found in U.S. patent Ser. No. 61/649,184, filed on May 18, 2012, entitled "CIRCUMSCRIBING DEFECTS IN OPTICAL DEVICES," which is hereby incorporated by reference in its entirety. In one implementation, the user can select any one or more of these putative defects to be mitigated using a user interface. When the user selects such defects, the X-Y stage may align the system to the defects by putting them in the center of the field of vision. At that location, the scribe laser is also aligned with the defect.

Once the defect for mitigation and the associated scribe diameter have been determined, the portable defect mitigator can execute the laser scribe to mitigate the defect. At step 1740, the portable defect mitigator mitigates the selected defect based on the selected scribe diameter. In some cases, an X-Y stage may be used to translate the focal point along the scribe pattern within the scribe diameter. In some cases, a dynamic autofocus system can be used to adjust the z-position of the focal point during scribe. For example, the dynamic autofocus system 1000 depicted in FIG. 11 can be used to determine any movement of the surface of the electrochromic device during mitigation. If the dynamic autofocus system 1000 determines that the surface has moved, typically due to window flexing, the system 1000 can adjust the lens to place the focal point back at the surface.

After the scribe has taken place, a confirmatory image may be captured to ensure that the defect has been appropriately mitigated, at step 1745. In this regard, the gradient of light intensity can be measured in the X or Y direction. A very steep gradient suggests that the remediation was effective. An un-remedied halo defect has a very gradual or diffuse variation in light intensity. After the remediation is completed at a particular location on the window, the defect mitigator may be disengaged by breaking vacuum and either put away or move to a different portion of the window, or even a different window in the vicinity, and used to remedy one or more additional defects.

In one embodiment, a pivot system is employed. The pivot system is designed to allow the detection and/or scribe optics to pivot such that the scribe laser can strike the surface of the electrochromic device at an angle deviating from the normal (i.e., an angle other than 90° from the plane of the device). Thus, the pivot system can be used to allow the optical system to be able to view and/or mitigate a defect under a spacer or a corner of an IGU.

The portable defect mitigator does not move as a whole during a typical defect identification and mitigation procedure. However, there may be vibration or another external force on the structure with the defect being mitigated that moves the structure with the portable defect mitigator attached during an identification and mitigation procedure. For example, there may be vibration from the wall or other building component to which the rail system in FIG. 5A is attached. In certain embodiments, active and/or passive vibration isolation can be used to isolate the portable defect mitigator from these forces. For example, components having materials and geometry tuned to dampen the predicted or measured vibrations can be used to passively isolate the portable defect mitigator from the vibrations. In an example using active stabilization, a gyroscope or pendulum may be used to actively stabilize the portable defect mitigator from the vibrations.

In one embodiment, the portable defect mitigator may include an optical system having a laser mitigating the defect, an optical detector (e.g., camera), and an illumination device that do not have the same co-axial optical path. In this embodiment, other mechanisms can be used to pair the focus of the laser, illumination device, and optical detector. By separating the optical path of one or more of these devices, the optics in these devices can be individualized optimized. In addition, by separating the optical path, there can be automated and independent movement of each device for focusing purposes. This can enable the individual design of different focusing characteristics, such as focal depth and area of focus, for each of the devices.

In one embodiment, a dynamic autofocus system may determine the distances to the deformed surfaces of an IGU. Based on these distances, the dynamic autofocus system may be able to determine the optical properties of the deformed surfaces of the IGU. The dynamic autofocus system may accommodate for these changes by adjusting the laser parameters used for mitigation. For example, the dynamic autofocus system may adjust the focal distance needed for the laser based on the optical properties of the deformed IGU surfaces.

One of ordinary skill in the art will appreciate that various combinations of the above embodiments are contemplated in this description. For example, apparatus 400 and/or 500 may include wireless communication components. In another example, apparatus 600 may travel on a rail system such as described in relation to FIG. 5B, even though apparatus 600 is smaller than the window pane upon which remediation is intended. In another example, apparatus 500 may be on a cart or table rather than a tripod. In yet another example, the identification mechanism and the mitigation mechanism may be apart from one another, not adjoining as depicted in the figures. In another example, the identification mechanism and the mitigation mechanism may have independent movement mechanisms. In yet another example, base 605 of apparatus 600 (see FIG. 7) may have a mechanism for rotating the identification mechanism and/or the mitigation mechanism. In yet another example, X-Y stages may have various configurations, methods of driving linear or rotation actuators and the like.

Although the foregoing has been described in some detail to facilitate understanding, the described embodiments are to be considered illustrative and not limiting. It will be apparent to one of ordinary skill in the art that certain changes and modifications can be practiced within the scope of the appended claims.

What is claimed is:

1. A portable defect mitigator for mitigating a defect in an electronic device of a window, the portable defect mitigator comprising:
   a first mechanism configured to detect the defect;
   a second mechanism configured to mitigate the defect;
   a dichroic mirror configured to receive collimated illumination from the first mechanism and collimated illumination from the second mechanism;
   a reflective mirror configured to receive collimated illumination from the first and second mechanisms along a coaxial path from the dichroic mirror; and
   a focal lens configured to receive collimated illumination reflected from the reflective mirror and configured to focus the collimated illumination to the electronic device to image and mitigate the defect.

2. The portable defect mitigator of claim 1, further comprising a pivoting mechanism configured to pivot the reflective mirror and the focal lens in coordinated rotational movement to focus the collimated illumination from the reflective mirror at an angle to a plane substantially parallel to a surface of the electronic device.

3. The portable defect mitigator of claim 1, wherein the focal lens is configured to focus the collimated illumination to a focal point at a corner of an insulated glass unit.

4. The portable defect mitigator of claim 1, wherein the focal lens is configured to focus the collimated illumination to a focal point under a spacer of an insulated glass unit.

5. The portable defect mitigator of claim 1, further comprising a light-tight, handheld chassis containing the first mechanism, the second mechanism, the reflective mirror, and the focal lens, the light-tight, handheld chassis adapted to affix to a surface of the window.

6. The portable defect mitigator of claim 1, wherein the portable defect mitigator weighs less than 10 lbs.

7. The portable defect mitigator of claim 1, further comprising a dynamic autofocus system for automatically focusing the second mechanism to a surface of the electronic device of a deforming window during defect mitigation.

8. The portable defect mitigator of claim 1, further comprising a stage, the dichroic mirror and the focal lens mounted to the stage, the stage configured to translate the dichroic mirror and the focal lens in coordinated movement in orthogonal directions in a plane parallel to a surface of the window.

9. The portable defect mitigator of claim 8, wherein the portable defect mitigator has a field of view of 22 mm×22 mm.

10. The portable defect mitigator of claim 1, further comprising a window thickness adjustment mechanism for initially focusing based on window parameters.

11. The portable defect mitigator of claim 10, wherein the window parameters include insulated glass unit thickness, spacer thickness, and pane thickness.

12. The portable defect mitigator of claim 1, wherein the first mechanism includes an illumination device and an optical detector.

13. The portable defect mitigator of claim 1, wherein the electronic device on the window is an electrochromic device.

14. The portable defect mitigator of claim 1, wherein the first mechanism comprises at least one of a microscope, a camera, and a photo detector, and wherein the second mechanism comprises at least one of a laser, a heat source, an induction coil, a microwave source, and a voltage source.

15. The portable defect mitigator of claim 1, wherein the dichroic mirror is configured to receive collimated illumination along a first direction from the first mechanism and collimated illumination along a second direction from the second mechanism.

* * * * *